US012264339B2

(12) United States Patent
Rubin et al.

(10) Patent No.: US 12,264,339 B2
(45) Date of Patent: *Apr. 1, 2025

(54) COMPOSITIONS AND METHODS INVOLVING ENGINEERED P27

(71) Applicant: THE REGENTS OF THE UNIVERSITY OF CALIFORNIA, Oakland, CA (US)

(72) Inventors: Seth Rubin, Santa Cruz, CA (US); Keelan Guiley, Santa Cruz, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/197,870

(22) Filed: May 16, 2023

(65) Prior Publication Data

US 2023/0407274 A1 Dec. 21, 2023

Related U.S. Application Data

(63) Continuation of application No. 16/977,441, filed as application No. PCT/US2019/026845 on Apr. 10, 2019, now Pat. No. 11,692,179.

(60) Provisional application No. 62/663,914, filed on Apr. 27, 2018.

(51) Int. Cl.
| C12N 9/12 | (2006.01) |
| C07K 14/47 | (2006.01) |
| C12Q 1/48 | (2006.01) |

(52) U.S. Cl.
CPC ............ *C12N 9/12* (2013.01); *C07K 14/4738* (2013.01); *C12Q 1/485* (2013.01); *C12Y 207/11022* (2013.01); *G01N 2440/14* (2013.01); *G01N 2500/02* (2013.01)

(58) Field of Classification Search
CPC ...... C12N 9/12; C07K 14/4738; C07K 19/00; C12Q 1/485; C12Y 207/11022; G01N 2440/14; G01N 2500/02
See application file for complete search history.

(56) References Cited

U.S. PATENT DOCUMENTS

| 11,692,179 B2 * | 7/2023 | Rubin ................ C07K 14/4738 435/15 |
| 2002/0068706 A1 | 6/2002 | Gyuris et al. |

FOREIGN PATENT DOCUMENTS

| WO | 2005040207 A1 | 5/2005 |

OTHER PUBLICATIONS

Gregg T., Mechanisms of β-Cell Compensation for Age and Obesity. Ph.D. Thesis, 2017, Univ. Wisconsin-Madison, pp. 1-134. (Year: 2017).*
"NCBI Blast Search Results with SID1", Jul. 12, 2022, 1 page.
U.S. Appl. No. 16/977,441, "Final Office Action", Nov. 10, 2022, 19 pages.
U.S. Appl. No. 16/977,441, "Non-Final Office Action", Jul. 19, 2022, 15 pages.
U.S. Appl. No. 16/977,441, "Notice of Allowance", Feb. 22, 2023, 8 pages.
Altschul et al., "Basic Local Alignment Search Tool", Journal of Molecular Biology, vol. 215, No. 3, Oct. 5, 1990, pp. 403-410.
Altschul et al., "Gapped BLAST and PSI-BLAST: A New Generation of Protein Database Search Programs", Nucleic Acids Research, vol. 25, No. 17, Sep. 1, 1997, pp. 3389-3402.
Bagui et al., "Analysis of Cyclin D3-CDK4 Complexes in Fibroblasts Expressing and Lacking P27 Kip1 and P21 Cip1", Molecular and Cellular Biology, vol. 20, No. 23, Dec. 2000, pp. 8748-8757.
Bagui et al., "P27Kip1 and P21Cip1 Are Not Required for the Formation of Active D Cyclin-Cdk4 Complexes", Molecular and Cellular Biology, vol. 23, No. 20, Oct. 2003, pp. 7285-7290.
Bullrich et al., "Chromosomal Mapping of Members of the cdc2 Family of Protein Kinases, cdk3, cdk6, PISSLRE, and PITALRE, and a cdk Inhibitor, p27Kip1, to Regions Involved in Human Cancer", Cancer Research, vol. 55, No. 6, Mar. 1995, pp. 1199-1205.
Cheng et al., "The p21Cip1 and p27Kip1 CDK 'Inhibitors' are Essential Activators of Cyclin D-dependent Kinases in Murine Fibroblasts", The European Molecular Biology Organization Journal, vol. 18, No. 6, Mar. 15, 1999, pp. 1571-1583.
Dick et al., "Molecular Mechanisms Underlying RB Protein Function", Nature Reviews Molecular Cell Biology, vol. 14, No. 5, Apr. 18, 2013, pp. 297-306.
Dickler et al., "MONARCH 1, a phase II study of abemaciclib, a CDK4 and CDK6 inhibitor, as a single agent, in patients with refractory HR+/HER2-metastatic breast cancer", Clinical Cancer Research, vol. 23, No. 17, Sep. 1, 2017, pp. 5218-5224.
Dyson, "RB1: A Prototype Tumor Suppressor and an Enigma", Genes & Development, vol. 30, No. 13, Jul. 1, 2016, pp. 1492-1502.
Finn et al., "Palbociclib and Letrozole in Advanced Breast Cancer", New England Journal of Medicine, vol. 375, No. 20, Nov. 17, 2016, pp. 1925-1936.
Grimmler et al., "Cdk-Inhibitory Activity and Stability of P27Kip1 are Directly Regulated by Oncogenic Tyrosine Kinases", Cell, vol. 128, No. 2, Jan. 26, 2007, pp. 269-280.
Hampl et al., "Levels and Interactions of p27, Cyclin D3, and CDK4 during the Formation and Maintenance of the Corpus Luteum in Mice", Biology of Reproduction, vol. 62, No. 5, May 1, 2000, pp. 1393-1401.
He et al., "Transient CDK4/6 Inhibition Protects Hematopoietic Stem Cells From Chemotherapy-Induced Exhaustion", Science Translational Medicine vol. 9, No. 387, Apr. 26, 2017, 27 pages.
James et al., "Differential Modification of P27Kip1 Controls its Cyclin D-Cdk4 Inhibitory Activity", Molecular and Cellular Biology, vol. 28, No. 1, Jan. 2008, pp. 498-510.

(Continued)

*Primary Examiner* — Ganapathirama Raghu
(74) *Attorney, Agent, or Firm* — Kilpatrick Townsend & Stockton LLP

(57) ABSTRACT

The disclosure provides polypeptides comprising an engineered p27, or a fragment thereof such polypeptides may be used to form trimeric protein complexes with a cyclin-dependent kinase 4 (Cdk4) (or a variant thereof) or Cdk6 (or a variant thereof), and a cyclin D (CycD) or a variant thereof.

19 Claims, 3 Drawing Sheets
Specification includes a Sequence Listing.

(56) References Cited

OTHER PUBLICATIONS

Kato et al., "Inactivation of the Cyclin D-dependent Kinase in the Rat Fibroblast Cell Line, 3Y1, Induced by Contact Inhibition", Journal of Biological Chemistry, vol. 272, No. 12, Mar. 21, 1997, pp. 8065-8070.

Labaer et al., "New Functional Activities for the P21 Family of CDK Inhibitors", Genes & Development, vol. 11, No. 7, Apr. 1, 1997, pp. 847-862.

Ladha et al., "Regulation of Exit From Quiescence by P27 and Cyclin D1-CDK4", Molecular and Cellular Biology vol. 18, No. 11, Nov. 1998, pp. 6605-6615.

Parry et al., "Cyclin D-CDK Subunit Arrangement is Dependent on the Availability of Competing INK4 and P21 Class Inhibitors", Molecular and Cellular Biology, vol. 19, No. 3, Mar. 1999, pp. 1775-1783.

Patel et al., "Brk/Protein Tyrosine Kinase 6 Phosphorylates p27KIP1, Regulating the Activity of Cyclin D-Cyclin-Dependent Kinase 4", Molecular and Cellular Biology, vol. 35, No. 9, May 2015, pp. 1506-1522.

PCT/US2019/026845, "International Preliminary Report on Patentability", Nov. 5, 2020, 8 pages.

PCT/US2019/026845, "International Search Report and Written Opinion", Jul. 15, 2019, 11 pages.

Qu et al., "Regulation of the Mammalian Cell Cycle: A model of the G1-to-S Transition", American Journal of Physiology: Cell Physiology, vol. 284, No. 2, Feb. 2002, pp. C349-C364.

Ray et al., "p27Kip1 Inhibits Cyclin D-Cyclin-Dependent Kinase 4 by Two Independent Modes", Molecular Cell Biology, vol. 29, No. 4, Feb. 2009, pp. 986-999.

Sadowski et al., "The Sequence-Structure Relationship and Protein Function Prediction", Current Opinion in Structural Biology vol. 19, Issue 3, Jun. 2009, pp. 357-362.

Seffernick et al., "Melamine Deaminase and Atrazine Chlorohydrolase: 98 Percent Identical but Functionally Different", Journal of Bacteriology, vol. 183, No. 8, 2001, pp. 2405-2410.

Sherr et al., "Targeting CDK4 and CDK6: From Discovery to Therapy", Cancer Discovery, vol. 6, No. 4, Apr. 2016, pp. 353-367.

Tang et al., "Identification of Dehalobacter Reductive Dehalogenases that Catalyse Dechlorination of Chloroform, 1,1,1-Trichloroethane and 1,1-Dichloroethane", Philosophical Transactions of the Royal Society B, vol. 368, Mar. 11, 2013, pp. 1-10.

Witkowski et al., "Conversion of a β-Ketoacyl Synthase to a Malonyl Decarboxylase by Replacement of the Active-Site Cysteine with Glutamine", Biochemistry, vol. 38, No. 36, 1999, pp. 11643-11650.

Xu et al., "Recent Advances of Highly Selective CDK4/6 Inhibitors in Breast Cancer", Journal of Hematology & Oncology, vol. 10, No. 1, Dec. 2017, pp. 1-12.

* cited by examiner

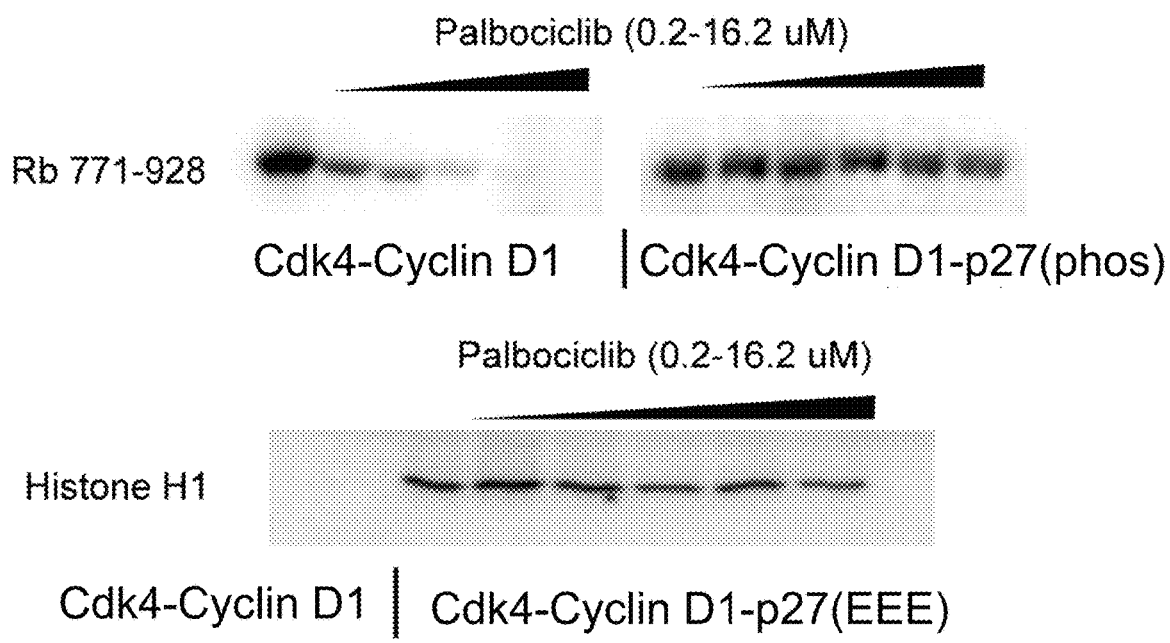

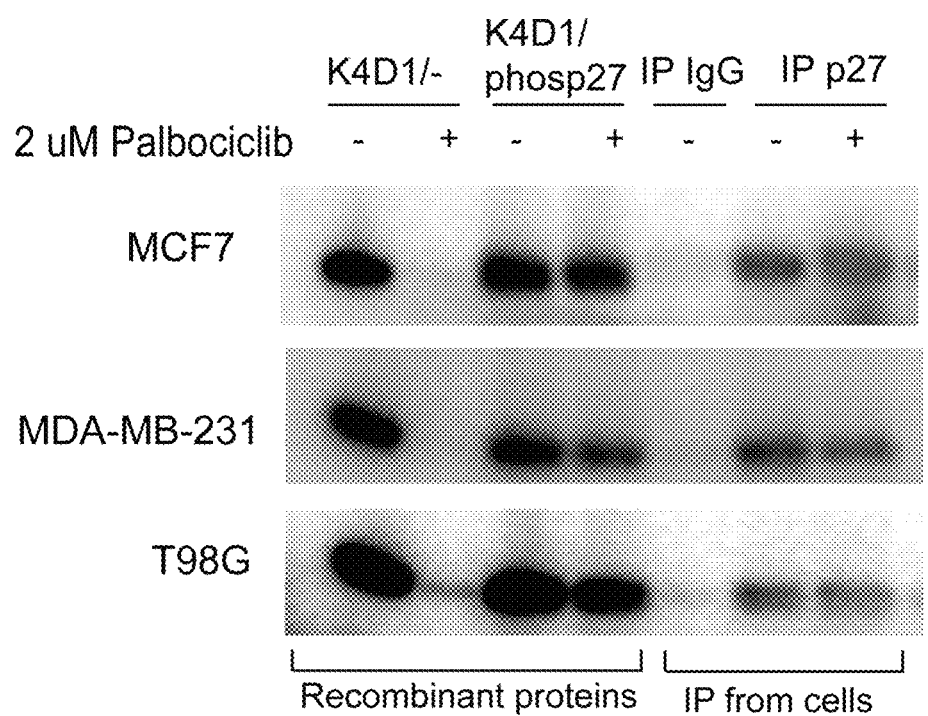

COMPOSITIONS AND METHODS INVOLVING ENGINEERED P27

CROSS-REFERENCES TO RELATED APPLICATIONS

This application is a continuation of U.S. application Ser. No. 16/977,441, filed Sep. 1, 2020, which is a National Stage of International Application No. PCT/US2019/026845, filed Apr. 10, 2019, which claims priority to U.S. Provisional Application No. 62/663,914, filed Apr. 27, 2018, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant Nos. CA132685 and CA206244, awarded by the National Institutes of Health. The government has certain rights in this invention.

REFERENCE TO A "SEQUENCE LISTING," A TABLE, OR A COMPUTER PROGRAM LISTING APPENDIX SUBMITTED ON A COMPACT DISK

This application contains a Sequence Listing submitted electronically and is hereby incorporated by reference in its entirety. The Sequence Listing.xml file is entitled 102913-001420US-1384635.xml is 108,380 bytes in size and was created on Aug. 25, 2023.

BACKGROUND

Cyclin-dependent kinases (Cdk) 4 and 6 promote cell proliferation through their kinase activity. Inhibitors of Cdk4 and Cdk6 may function as cancer therapeutics. The active cellular form of the enzyme Cdk4 or Cdk6 is in complex with cyclin D (CycD) and p27. Current inhibitors of Cdk4/6 were developed using Cdk4-CycD dimeric complexes that lack p27, in part because of the technical challenges in generating the active form of p27. However, the Cdk4-CycD dimeric complex does not readily form in all cells. Further, certain complexes including p27 may be resistant to treatments.

SUMMARY

In one aspect, the disclosure features a polypeptide comprising an engineered p27, or a fragment thereof, wherein the engineered p27 has at least one amino acid substitution at a position selected from the group consisting of Y74, Y88, and Y89, wherein the engineered p27 forms a trimeric protein complex with (i) a cyclin-dependent kinase 4 (Cdk4) or a variant thereof, or a Cdk6 or a variant thereof, and (ii) a cyclin D (CycD) or a variant thereof, and wherein the amino acid positions are determined with reference to the sequence of SEQ ID NO: 1.

In some embodiments, the engineered p27 comprises amino acid substitution Y74E or Y74D. In some embodiments, the engineered p27 comprises amino acid substitution Y74E, Y74D, or Y74R. In some embodiments, the engineered p27 comprises amino acid substitution Y88E or Y88D. In some embodiments, the engineered p27 comprises amino acid substitution Y89E or Y89D.

In some embodiments of this aspect, the engineered p27 comprises a sequence having at least 90% sequence identity to the sequence of SEQ ID NO: 1.

In some embodiments of this aspect, the engineered p27 comprises a sequence of KPSACRNLFGPVDHEEL-TRDLEKHCRDMEEASQRKWNFDFQNHKPLEGKX-iEWQEVE KGSLPEFX$_2$X$_3$RPPRPPKGA (SEQ ID NO: 59), wherein X$_1$ is Y, E, D, or R; X$_2$ is Y, E, or D; and X$_3$ is Y, E, or D, and wherein at least one of X$_1$, X$_2$, and X$_3$ is not Y. In some embodiments, X$_1$ is Y. In some embodiments, X$_1$ is E. In some embodiments, X$_1$ is D. In some embodiments, X$_1$ is R. In some embodiments, X$_2$ is Y. In some embodiments, X$_2$ is E. In some embodiments, X$_2$ is D. In some embodiments, X$_3$ is Y. In some embodiments, X$_3$ is E. In some embodiments, X$_3$ is D.

In some embodiments of this aspect, the engineered p27 comprises a sequence having at least 90% sequence identity to the sequence of (SEQ ID NO: 6)
KPSACRNLFGPVDHEELTRDLEKHCRDMEEASQRKWNFDFQNHKPLEGKE

EWQEVEKGSLPEFYYRPPRPPKGA or (SEQ ID NO: 4)
MSNVRVSNGSPSLERMDARQAEHPKPSACRNLFGPVDHEELTRDLEKHCR

DMEEASQRKWNFDFQNHKPLEGKEEWQEVEKGSLPEFYYRPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 12)
KPSACRNLFGPVDHEELTRDLEKHCRDMEEASQRKWNFDFQNHKPLEGK

REWQEVEKGSLPEFYYRPPRPPKGA or (SEQ ID NO: 10)
MSNVRVSNGSPSLERMDARQAEHPKPSACRNLFGPVDHEELTRDLEKHC

RDMEEASQRKWNFDFQNHKPLEGKREWQEVEKGSLPEFYYRPPRPPKGA

CKVPAQESQDVSGSRPAAPLIGAPANSEDTHLVDPKTDPSDSQTGLAEQ

CAGIRKRPATDDSSTQNKRANRTEENVSDGSPNAGSVEQTPKKPGLRRR

QT.

In some embodiments of this aspect, the engineered p27 comprises a sequence having at least 90% sequence identity to the sequence of (SEQ ID NO: 15)
KPSACRNLFGPVDHEELTRDLEKHCRDMEEASQRKWNFDFQNHKPLEGKY

EWQEVEKGSLPEFYRPPRPPKGA or (SEQ ID NO: 13)
MSNVRVSNGSPSLERMDARQAEHPKPSACRNLFGPVDHEELTRDLEKHCR

DMEEASQRKWNFDFQNHKPLEGKYEWQEVEKGSLPEFYRPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 21)
KPSACRNLFGPVDHEELTRDLEKHCRDMEEASQRKWNFDFQNHKPLEGKY

EWQEVEKGSLPEFYERPPRPPKGA or (SEQ ID NO: 19)
MSNVRVSNGSPSLERMDARQAEHPKPSACRNLFGPVDHEELTRDLEKHCR

DMEEASQRKWNFDFQNHKPLEGKYEWQEVEKGSLPEFYERPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 27)
KPSACRNLFGPVDHEELTRDLEKHCRDMEEASQRKWNFDFQNHKPLEGKE

EWQEVEKGSLPEFEYRPPRPPKGA or (SEQ ID NO: 25)
MSNVRVSNGSPSLERMDARQAEHPKPSACRNLFGPVDHEELTRDLEKHCR

DMEEASQRKWNFDFQNHKPLEGKEEWQEVEKGSLPEFEYRPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 30)
KPSACRNLFGPVDHEELTRDLEKHCRDMEEASQRKWNFDFQNHKPLEGK

EEWQEVEKGSLPEFYERPPRPPKGA or (SEQ ID NO: 28)
MSNVRVSNGSPSLERMDARQAEHPKPSACRNLFGPVDHEELTRDLEKHC

RDMEEASQRKWNFDFQNHKPLEGKEEWQEVEKGSLPEFYERPPRPPKGA

CKVPAQESQDVSGSRPAAPLIGAPANSEDTHLVDPKTDPSDSQTGLAEQ

CAGIRKRPATDDSSTQNKRANRTEENVSDGSPNAGSVEQTPKKPGLRRR

QT.

In some embodiments of this aspect, the engineered p27 comprises a sequence having at least 90% sequence identity to the sequence of (SEQ ID NO: 33)
KPSACRNLFGPVDHEELTRDLEKHCRDMEEASQRKWNFDFQNHKPLEGK

YEWQEVEKGSLPEFEERPPRPPKGA or (SEQ ID NO: 31)
MSNVRVSNGSPSLERMDARQAEHPKPSACRNLFGPVDHEELTRDLEKHC

RDMEEASQRKWNFDFQNHKPLEGKYEWQEVEKGSLPEFEERPPRPPKGA

CKVPAQESQDVSGSRPAAPLIGAPANSEDTHLVDPKTDPSDSQTGLAEQ

CAGIRKRPATDDSSTQNKRANRTEENVSDGSPNAGSVEQTPKKPGLRRR

QT.

In some embodiments of this aspect, the engineered p27 comprises a sequence having at least 90% sequence identity to the sequence of (SEQ ID NO: 36)
KPSACRNLFGPVDHEELTRDLEKHCRDMEEASQRKWNFDFQNHKPLEGKE

EWQEVEKGSLPEFEERPPRPPKGA or (SEQ ID NO: 34)
MSNVRVSNGSPSLERMDARQAEHPKPSACRNLFGPVDHEELTRDLEKHCR

DMEEASQRKWNFDFQNHKPLEGKEEWQEVEKGSLPEFEERPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In another aspect, the disclosure features a trimeric protein complex comprising: (i) a polypeptide comprising an engineered p27 as described in the previous aspect, or a phosphorylated, wild-type p27 or a fragment thereof; (ii) a Cdk4 or a variant thereof, or a Cdk6 or a variant thereof; and (iii) a CycD or a variant thereof, wherein the Cdk4 or the variant thereof or the Cdk6 or the variant thereof in the trimeric protein complex is an active kinase.

In some embodiments of this aspect, the Cdk4 or the variant thereof or the Cdk6 or the variant thereof is capable of phosphorylating a protein comprising a phosphorylation site having the sequence $X_1PX_2X_3$ (SEQ ID NO: 60), wherein $X_1$ is S or T; $X_2$ is any amino acid; and $X_3$ is K or R. In some embodiments, the protein comprising the phosphorylation site is retinoblastoma protein (Rb), FoxM1, or histone H1.

In some embodiments of this aspect, the CycD is CycD1, CycD2, CycD3, or a variant thereof.

In some embodiments of this aspect, the CycD1 or the variant thereof comprises a sequence having at least 90% sequence identity to the sequence of (SEQ ID NO: 55)
MEHQLLCCEVETIRRAYPDANLLNDRVLRAMLKAEETCAPSVSYFKCVQK

EVLPSMRKIVATWMLEVCEEQKCEEEVFPLAMNYLDRFLSLEPVKKSRLQ

LLGATCMFVASKMKETIPLTAEKLCIYTDNSIRPEELLQMELLLVNKLKW

NLAAMTPHDFIEHFLSKMPEAEENKQIIRKHAQTFVALCATDVKFISNPP

SMVAAGSVVAAVQGLNLRSPNNFLSYYRLTRFLSRVIKCDPDCLRACQEQ

IEALLESSLRQAQQNMDPKAAEEEEEEEEVDLACTPTDVRDVDI, or (SEQ ID NO: 56)
DANLLNDRVLRAMLKAEETCAPSVSYFKCVQKEVLPSMRKIVATWMLEVC

EEQKCEEEVFPLAMNYLDRFLSLEPVKKSRLQLLGATCMFVASKMKETIP

LTAEKLCIYTDNSIRPEELLQMELLLVNKLKWNLAAMTPHDFIEHFLSKM

PEAEENKQIIRKHAQTFVALCATDVKFISNPPSMVAAGSVVAAVQGLNLR

SPNNFLSYYRLTRFLSRVIKCDPDCLRACQEQIEALLESSLRQAQQNMD.

In some embodiments of this aspect, the CycD2 comprises a sequence having at least 90% sequence identity to the sequence of (SEQ ID NO: 57)
MELLCHEVDPVRRAVRDRNLLRDDRVLQNLLTIEERYLPQCSYFKCVQKD
IQPYMRRMVATWMLEVCEEQKCEEEVFPLAMNYLDRFLAGVPTPKSHLQL
LGAVCMFLASKLKETSPLTAEKLCIYTDNSIKPQELLEWELVVLGKLKWN
LAAVTPHDFIEHILRKLPQQREKLSLIRKHAQTFIALCATDFKFAMYPPS
MIATGSVGAAICGLQQDEEVSSLTCDALTELLAKITNTDVDCLKACQEQI
EAVLLNSLQQYRQDQRDGSKSEDELDQASTPTDVRDIDL.

In some embodiments of this aspect, the CycD3 comprises a sequence having at least 90% sequence identity to the sequence of (SEQ ID NO: 58)
MELLCCEGTRHAPRAGPDPRLLGDQRVLQSLLRLEERYVPRASYFQCVQR
EIKPHMRKMLAYWMLEVCEEQRCEEEVFPLAMNYLDRYLSCVPTRKAQLQ
LLGAVCMLLASKLRETTPLTIEKLCIYTDHAVSPRQLRDWEVLVLGKLKW
DLAAVIAHDFLAFILHRLSLPRDRQALVKKHAQTFLALCATDYTFAMYPP
SMIATGSIGAAVQGLGACSMSGDELTELLAGITGTEVDCLRACQEQIEAA
LRESLREASQTSSSPAPKAPRGSSSQGPSQTSTPTDVTAIHL.

In some embodiments of this aspect, the Cdk4 or a variant thereof comprises a sequence having at least 90% sequence identity to the sequence of (SEQ ID NO: 37)
MATSRYEPVAEIGVGAYGTVYKARDPHSGHFVALKSVRVPNGGGGGGLP
ISTVREVALLRRLEAFEHPNVVRLMDVCATSRTDREIKVTLVFEHVDQDL
RTYLDKAPPPGLPAETIKDLMRQFLRGLDFLHANCIVHRDLKPENILVTS
GGTVKLADFGLARIYSYQMALTPVVVTLWYRAPEVLLQSTYATPVDMWSV
GCIFAEMFRRKPLFCGNSEADQLGKIFDLIGLPPEDDWPRDVSLPRGAFP
PRGPRPVQSVVPEMEESGAQLLLEMLTFNPHKRISAFRALQHSYLHKDEG
NPE.

In some embodiments of this aspect, the variant of Cdk4 comprises T172E or T172D, and the amino acid positions are determined with reference to the sequence of SEQ ID NO: 37. In some embodiments, the variant of Cdk4 comprises a sequence having at least 90% sequence identity to the sequence of (SEQ ID NO: 39)
MATSRYEPVAEIGVGAYGTVYKARDPHSGHFVALKSVRVPNGGGGGGLP
ISTVREVALLRRLEAFEHPNVVRLMDVCATSRTDREIKVTLVFEHVDQDL
RTYLDKAPPPGLPAETIKDLMRQFLRGLDFLHANCIVHRDLKPENILVTS
GGTVKLADFGLARIYSYQMALEPVVVTLWYRAPEVLLQSTYATPVDMWSV
GCIFAEMFRRKPLFCGNSEADQLGKIFDLIGLPPEDDWPRDVSLPRGAFP
PRGPRPVQSVVPEMEESGAQLLLEMLTFNPHKRISAFRALQHSYLHKDEG
NPE,
or (SEQ ID NO: 38)
MATSRYEPVAEIGVGAYGTVYKARDPHSGHFVALKSVRVPNGGGGGGLP
ISTVREVALLRRLEAFEHPNVVRLMDVCATSRTDREIKVTLVFEHVDQDL
RTYLDKAPPPGLPAETIKDLMRQFLRGLDFLHANCIVHRDLKPENILVTS
GGTVKLADFGLARIYSYQMALDPVVVTLWYRAPEVLLQSTYATPVDMWSV
GCIFAEMFRRKPLFCGNSEADQLGKIFDLIGLPPEDDWPRDVSLPRGAFP
PRGPRPVQSVVPEMEESGAQLLLEMLTFNPHKRISAFRALQHSYLHKDEG
NPE.

In some embodiments of this aspect, the variant of Cdk4 has amino acid residues 44 to 46 deleted, G43E or G43D, and G47E or G47D, and the amino acid positions are determined with reference to the sequence of SEQ ID NO: 37. In some embodiments, the variant of Cdk4 comprises a sequence having at least 90% sequence identity to the sequence of (SEQ ID NO: 42)
MATSRYEPVAEIGVGAYGTVYKARDPHSGHFVALKSVRVPNGEDGLPIST
VREVALLRRLEAFEHPNVVRLMDVCATSRTDREIKVTLVFEHVDQDLRTY
LDKAPPPGLPAETIKDLMRQFLRGLDFLHANCIVHRDLKPENILVTSGGT
VKLADFGLARIYSYQMALTPVVVTLWYRAPEVLLQSTYATPVDMWSVGCI
FAEMFRRKPLFCGNSEADQLGKIFDLIGLPPEDDWPRDVSLPRGAFPPRG
PRPVQSVVPEMEESGAQLLLEMLTFNPHKRISAFRALQHSYLHKDEGNP
E, (SEQ ID NO: 41)
MATSRYEPVAEIGVGAYGTVYKARDPHSGHFVALKSVRVPNGDEGLPISTV
REVALLRRLEAFEHPNVVRLMDVCATSRTDREIKVTLVFEHVDQDLRTYLD
KAPPPGLPAETIKDLMRQFLRGLDFLHANCIVHRDLKPENILVTSGGTVKL
ADFGLARIYSYQMALTPVVVTLWYRAPEVLLQSTYATPVDMWSVGCIFAEM
FRRKPLFCGNSEADQLGKIFDLIGLPPEDDWPRDVSLPRGAFPPRGPRPVQ
SVVPEMEESGAQLLLEMLTFNPHKRISAFRALQHSYLHKDEGNPE, (SEQ ID NO: 40)
MATSRYEPVAEIGVGAYGTVYKARDPHSGHFVALKSVRVPNGEEGLPISTV
REVALLRRLEAFEHPNVVRLMDVCATSRTDREIKVTLVFEHVDQDLRTYLD
KAPPPGLPAETIKDLMRQFLRGLDFLHANCIVHRDLKPENILVTSGGTVKL
ADFGLARIYSYQMALTPVVVTLWYRAPEVLLQSTYATPVDMWSVGCIFAEM
FRRKPLFCGNSEADQLGKIFDLIGLPPEDDWPRDVSLPRGAFPPRGPRPVQ
SVVPEMEESGAQLLLEMLTFNPHKRISAFRALQHSYLHKDEGNPE,
or (SEQ ID NO: 43)
MATSRYEPVAEIGVGAYGTVYKARDPHSGHFVALKSVRVPNGDDGLPISTV
REVALLRRLEAFEHPNVVRLMDVCATSRTDREIKVTLVFEHVDQDLRTYLD
KAPPPGLPAETIKDLMRQFLRGLDFLHANCIVHRDLKPENILVTSGGTVKL
ADFGLARIYSYQMALTPVVVTLWYRAPEVLLQSTYATPVDMWSVGCIFAEM
FRRKPLFCGNSEADQLGKIFDLIGLPPEDDWPRDVSLPRGAFPPRGPRPVQ
SVVPEMEESGAQLLLEMLTFNPHKRISAFRALQHSYLHKDEGNPE.

In some embodiments of this aspect, the variant of Cdk4 has amino acid residues 44 to 46 deleted, G43E or G43D, G47E or G47D, and T172E or T172D, wherein the amino acid positions are determined with reference to the sequence of SEQ ID NO: 37. In some embodiments, the variant of Cdk4 comprises a sequence having at least 90% sequence identity to the sequence of (SEQ ID NO: 48)
MATSRYEPVAEIGVGAYGTVYKARDPHSGHFVALKSVRVPNGEEGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALEPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E,
or (SEQ ID NO: 44)
MATSRYEPVAEIGVGAYGTVYKARDPHSGHFVALKSVRVPNGEEGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALDPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E.

In some embodiments of this aspect, the Cdk6 comprises a sequence having at least 90% sequence identity to the sequence of (SEQ ID NO: 52)
MEKDGLCRADQQYECVAEIGEGAYGKVFKARDLKNGGRFVALKRVRVQTG

EEGMPLSTIREVAVLRHLETFEHPNVVRLFDVCTVSRTDRETKLTLVFEH

VDQDLTTYLDKVPEPGVPTETIKDMMFQLLRGLDFLHSHRVVHRDLKPQN

ILVTSSGQIKLADFGLARIYSFQMALTSVVVTLWYRAPEVLLQSSYATPV

DLWSVGCIFAEMFRRKPLFRGSSDVDQLGKILDVIGLPGEEDWPRDVALP

RQAFHSKSAQPIEKFVTDIDELGKDLLLKCLTFNPAKRISAYSALSHPYF

QDLERCKENLDSHLPPSQNTSELNTA.

In some embodiments of this aspect, the variant of Cdk6 comprises T177E or T177D, wherein the amino acid positions are determined with reference to the sequence of SEQ ID NO: 52. In some embodiments, the variant of Cdk6 comprises a sequence having at least 90% sequence identity to the sequence of (SEQ ID NO: 54)
MEKDGLCRADQQYECVAEIGEGAYGKVFKARDLKNGGRFVALKRVRVQTG

EEGMPLSTIREVAVLRHLETFEHPNVVRLFDVCTVSRTDRETKLTLVFEH

VDQDLTTYLDKVPEPGVPTETIKDMMFQLLRGLDFLHSHRVVHRDLKPQN

ILVTSSGQIKLADFGLARIYSFQMALESVVVTLWYRAPEVLLQSSYATPV

DLWSVGCIFAEMFRRKPLFRGSSDVDQLGKILDVIGLPGEEDWPRDVALP

RQAFHSKSAQPIEKFVTDIDELGKDLLLKCLTFNPAKRISAYSALSHPYF

QDLERCKENLDSHLPPSQNTSELNTA,
or (SEQ ID NO: 53)
MEKDGLCRADQQYECVAEIGEGAYGKVFKARDLKNGGRFVALKRVRVQTG

EEGMPLSTIREVAVLRHLETFEHPNVVRLFDVCTVSRTDRETKLTLVFEH

VDQDLTTYLDKVPEPGVPTETIKDMMFQLLRGLDFLHSHRVVHRDLKPQN

ILVTSSGQIKLADFGLARIYSFQMALDSVVVTLWYRAPEVLLQSSYATPV

DLWSVGCIFAEMFRRKPLFRGSSDVDQLGKILDVIGLPGEEDWPRDVALP

RQAFHSKSAQPIEKFVTDIDELGKDLLLKCLTFNPAKRISAYSALSHPYF

QDLERCKENLDSHLPPSQNTSELNTA.

In some embodiments of this aspect, the phosphorylated, wild-type p27 or a fragment thereof comprises the sequence of any one of SEQ ID NOS: 1-3 and is phosphorylated at Y74, Y88, and/or Y89, in which the amino acid positions are determined with reference to the sequence of SEQ ID NO: 1.

In another aspect, the disclosure features a method of screening for inhibitors of a trimeric protein complex comprising an active Cdk4 or a variant thereof, or an active Cdk6 or a variant thereof, comprising: (a) providing a trimeric protein complex described in the previous aspect; (b) contacting the trimeric protein complex with a compound and a substrate of the Cdk4 or the variant thereof or the Cdk6 or the variant thereof, and (c) determining the phosphorylation status of the substrate, wherein the compound is an inhibitor of the trimeric protein complex if the compound inhibits the phosphorylation activity of the Cdk4 or the variant thereof or the Cdk6 or the variant thereof.

In some embodiments of this aspect, the method further comprises, prior to step (a), phosphorylating a wild-type p27 or a fragment thereof by contacting the wild-type p27 with a kinase. In some embodiments, the kinase is selected from the group consisting of Brk kinase, Src kinase, and Abl kinase.

In some embodiments of this aspect, the method further comprises, after step (c), comparing the phosphorylation status of the substrate with the phosphorylation status of the substrate when the compound is not present.

In some embodiments of this aspect, the substrate comprises a phosphorylation site having the sequence $X_1PX_2X_3$ (SEQ ID NO: 60), wherein $X_1$ is S or T; $X_2$ is any amino acid; and $X_3$ is K or R. In some embodiments, the substrate comprising the phosphorylation site is Rb, FoxM1, histone H1, or a variant thereof.

In another aspect, the disclosure features a method of expressing and purifying a trimeric protein complex comprising (i) a phosphorylated, wild-type p27 or a fragment thereof, (ii) a Cdk4 or a variant thereof or a Cdk6 or a variant thereof, and (iii) a CycD or a variant thereof, the method comprising: (a) expressing the Cdk4 or the variant thereof or the Cdk6 or the variant thereof, and the CycD or the variant thereof in a first cell line, where the first cell line comprises one or more expression vectors configured to express the Cdk4 or the variant thereof or the Cdk6 or the variant thereof, and the CycD or the variant thereof, (b) expressing the wild-type p27 or the fragment thereof in a second cell line, where the second cell line comprises an expression vector configured to express the wild-type p27 or the fragment thereof, (c) purifying the Cdk4 or the variant thereof or the Cdk6 or the variant thereof, and the CycD or the variant thereof from the first cell line and the wild-type p27 or the fragment thereof from the second cell line; (d) phosphorylating the wild-type p27 or the fragment thereof obtained from step (c) with a kinase; and (e) combining the phosphorylated, wild-type p27 or the fragment thereof obtained from step (d) with the purified Cdk4 or the variant thereof or the purified Cdk6 or the variant thereof, and the CycD or the variant thereof obtained from step (c) under conditions that allow the formation of the trimeric protein complex, wherein the Cdk4 or the variant thereof or the Cdk6 or the variant thereof in the trimeric protein complex is an active kinase.

In some embodiments of this aspect, the expression vector is a baculovirus vector. In some embodiments, the first and/or second cell line is an insect cell line.

BRIEF DESCRIPTION OF THE DRAWINGS

FIG. 1C shows a summary of kinetic results. The engineered p27 with Y74E, Y88E, and Y89E-Cdk4-CycD1 trimeric complex enhances ATP substrate capture and has a greater activity toward FoxM1 and histone 1.

FIG. 1D shows the wild-type p27-Cdk4-CycD1 trimeric complex with phosphorylated p27 and engineered p27 with Y74E, Y88E, and Y89E-Cdk4-CycD1 trimeric complex are poorly inhibited by palbociclib.

FIG. 1E shows the endogenous p27-Cdk4-CycD1 trimeric complex immunoprecipitated from cells was not sensitive to palbociclib inhibition.

DETAILED DESCRIPTION OF THE EMBODIMENTS

I. Introduction

Figure 1A:
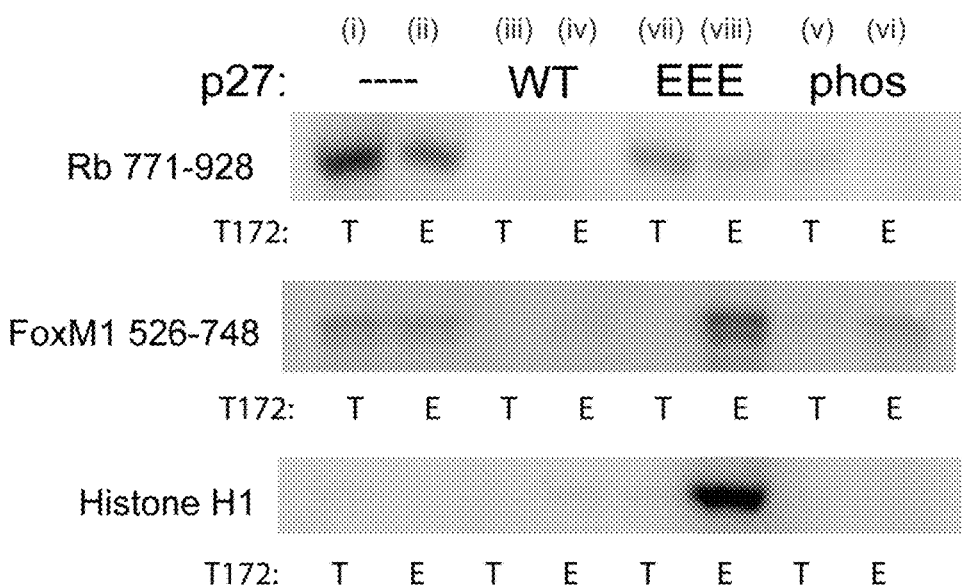
FIG. 1A shows $^{32}$P-ATP labeling of the indicated substrate with each of complexes (i)-(viii) as described in Example 3 (WT: wild-type, EEE: Y74E, Y88E, and Y89E substitutions in p27, phos: Brk-phosphorylated p27).

Genetic and biochemical studies have demonstrated that the retinoblastoma protein (Rb) pathway is a major regulator of cell cycle progression in G1 phase[1,2]. In G0/G1 phase, Rb and its family members p107 and p130 inhibit the E2F family of transcription factors (e.g., E2F1-5). In response to mitogenic signals, cyclin-dependent kinase (Cdk)-cyclin complexes phosphorylate Rb family members, which results in the disruption of complexes between Rb and E2F family members and allows the transcription of genes essential for S-phase progression. Cdk-cyclin complexes, e.g., Cdk4/6-CycD and Cdk2-CycE/A, are inhibited by proteins from the p16 family and can be either inhibited or activated by proteins from the p27 (p21, p27, p57) family.

With the goal of preventing Rb inactivation and cancer cell-cycle progression, specific inhibitors of Cdk4 and/or Cdk6 have been developed in the past decade. These inhibitors were found in screens against recombinant Cdk4-CycD dimeric complex. One of these inhibitors, palbociclib, was approved in 2015 for the treatment of estrogen receptor-positive breast cancer[3-5]. Several other Cdk4/6 inhibitors are being tested (e.g., ribociclib, abemaciclib, trilaciclib) in multiple cancer types[6-8]. Key unresolved challenges limiting Cdk4/6 inhibitors are, e.g., mechanisms of inherent resistance, acquired resistance, and early adaptation.

The activity of p27 (also known as cyclin-dependent kinase inhibitor 1B) towards Cdk4/6 is complex. p27 inhibits Cdk4/6-CycD activity in vitro and in cells under conditions of growth arrest[9-13]. At the same time, however, p27 increases Cdk4/6-CycD stability and is always present in active Cdk4/6-CycD complexes that phosphorylate Rb in proliferating cells[14-18]. Phosphorylation of p27 by tyrosine kinases (e.g., Src kinase, Brk kinase, Abl kinase) on amino acid residues Y74, Y88, and Y89 of p27 further increases Cdk4/6 activity, and this phosphorylation has been suggested to switch p27 from an inhibitor to an activator[19-21].

Disclosed herein are the structure and activity of the p27-Cdk4/6-CycD complex. Also disclosed is a method of expressing and purifying an active, recombinant p27-Cdk4/6-CycD complex.

In some embodiments, the method involves treating p27 with an active kinase (e.g., tyrosine kinase) such as recombinant Brk, Src, or Abl kinases. In some aspects of this embodiment, the p27 is treated prior to assembly of the enzyme. In other embodiments, the method involves using a p27 polypeptide that comprises a mutation at Y74, a mutation at Y88, and/or a mutation at Y89, or any combination thereof. In some aspects of this embodiment, the p27 polypeptide comprises a Y74E mutation and no mutation at Y88 or Y89. In other aspects, the p27 polypeptide comprises a Y88E mutation and a Y89E mutation In other aspects, the p27 polypeptide comprises a Y74R mutation, a Y88E mutation, and a Y89E mutation. It is disclosed herein that p27-activated Cdk4-CycD complex: (1) has broader substrate specificity than the Cdk4-CycD dimeric complex and (2) is resistant to treatment of palbociclib. For these reasons, the p27-Cdk4/6-CycD enzyme complex may be used for screening of new inhibitors that are effective in different cancer types.

II. Definitions

As used herein, the term "engineered p27" refers to a p27 polypeptide that contains one or more amino acid substitutions, additions, and/or deletions relative to the amino acid sequence of a wild-type p27 (e.g., SEQ ID NO: 1). An engineered p27 may have the same length as a wild-type p27 or may be a fragment of the wild-type p27. An engineered p27 as described herein may have at least one amino acid substitution at a position selected from the group consisting of Y74, Y88, and Y89, in which the amino acid positions are determined with reference to the sequence of SEQ ID NO: 1. Further, an engineered p27 as described herein forms a trimeric protein complex with a cyclin-dependent kinase 4 (Cdk4) or a variant thereof, or Cdk6 or a variant thereof, and a cyclin D (CycD) or a variant thereof.

As used herein, the term "Cdk4 or a variant thereof" refers to a wild-type cyclin-dependent kinase 4 (Cdk4) or a variant of the wild-type Cdk4. A wild-type Cdk4 may have the sequence of SEQ ID NO: 37. A variant of the wild-type Cdk4 (also called Cdk4 variant) refers to a Cdk4 that contains one or more amino acid substitutions, additions, and/or deletions relative to the amino acid sequence of the wild-type Cdk4 (e.g., SEQ ID NO: 37). A Cdk4 variant may have the same length as a wild-type Cdk4 or may be a fragment of the wild-type Cdk4. A Cdk4 variant as described herein is capable of phosphorylation activity and can form a trimeric complex with a CycD or a variant thereof, and an engineered p27 or a wild-type p27.

An active Cdk4 or a variant thereof as used herein refers to a Cdk4 or a variant thereof that is an active kinase and is capable of phosphorylating at a phosphorylation site, e.g., a phosphorylation site having the sequence $X_1PX_2X_3$ (SEQ ID NO: 60), wherein $X_1$ is S or T; $X_2$ is any amino acid; and $X_3$ is K or R.

As used herein, the term "Cdk6 or a variant thereof" refers to a wild-type cyclin-dependent kinase 6 (Cdk6) or a variant of the wild-type Cdk6. A wild-type Cdk6 may have the sequence of SEQ ID NO: 52. A variant of the wild-type Cdk6 (also called Cdk6 variant) refers to a Cdk6 that contains one or more amino acid substitutions, additions, and/or deletions relative to the amino acid sequence of the wild-type Cdk6 (e.g., SEQ ID NO: 52). A Cdk6 variant may have the same length as a wild-type Cdk6 or may be a fragment of the wild-type Cdk6. A Cdk6 variant as described herein is capable of phosphorylation activity and can form a trimeric complex with a CycD or a variant thereof, and an engineered p27 or a wild-type p27. An active Cdk6 or a variant thereof as used herein refers to a Cdk6 or a variant thereof that is an active kinase and is capable of phosphorylating at a phosphorylation site, e.g., a phosphorylation site having the sequence $X_1PX_2X_3$ (SEQ ID NO: 60), wherein $X_1$ is S or T; $X_2$ is any amino acid; and $X_3$ is K or R.

As used herein, the term "cyclin D (CycD) or a variant thereof" refers to a wild-type CycD or a variant of the wild-type CycD (also called CycD variant) that is capable of forming a trimeric protein complex described herein comprising an active Cdk4 (or a variant thereof) or Cdk6 (or a variant thereof). A wild-type CycD may be a wild-type CycD1, CycD2, or CycD3. A trimeric protein complex describe herein may comprise any one of the CycD1, CycD2, CycD3, or a variant thereof described herein.

As used herein, the term "trimeric protein complex" or "trimeric complex" refers to a complex formed by three proteins: (i) an engineered p27 or wild-type p27; (ii) a Cdk4 (or a variant thereof) or Cdk6 (or a variant thereof); and (iii) a cyclin D (CycD) (or a variant thereof).

As used herein, the term "percent (%) sequence identity" refers to the percentage of amino acid or nucleic acid residues of a candidate sequence that are identical to the amino acid or nucleic acid residues of a reference sequence after aligning the sequences and introducing gaps, if necessary, to achieve the maximum percent identity (i.e., gaps can be introduced in one or both of the candidate and reference sequences for optimal alignment). In some embodiments, percent sequence identity can be any integer from 50% to 100%. In some embodiments, a sequence is substantially identical to a reference sequence if the sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned.

Alignment for purposes of determining percent sequence identity can be achieved in various ways that are within the skill in the art, for instance, using publicly available computer software such as BLAST, ALIGN, or Megalign (DNASTAR) software. The BLAST and BLAST 2.0 algorithms are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. Those skilled in the art can determine appropriate parameters for measuring alignment, including any algorithms needed to achieve maximal alignment over the full length of the sequences being compared. In some embodiments, the percent amino acid or nucleic acid sequence identity of a given candidate sequence to, with, or against a given reference sequence (which can alternatively be phrased as a given candidate sequence that has or includes a certain percent amino acid or nucleic acid sequence identity to, with, or against a given reference sequence) is calculated as follows:

$$100 \times (\text{fraction of } A/B)$$

where A is the number of amino acid or nucleic acid residues scored as identical in the alignment of the candidate sequence and the reference sequence, and where B is the total number of amino acid or nucleic acid residues in the reference sequence. In some embodiments where the length of the candidate sequence does not equal to the length of the reference sequence, the percent amino acid or nucleic acid sequence identity of the candidate sequence to the reference sequence would not equal to the percent amino acid or nucleic acid sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid or nucleic acid residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid or nucleic acid residue as the corresponding position in the reference sequence, then the molecules are identical at that position.

III. Trimeric Protein Complex

In response to mitogenic signals, complexes involving p27, Cdk4 or Cdk6, and cyclin D (CycD) phosphorylate retinoblastoma protein (Rb), leading to the transcription of genes essential for S-phase cell cycle progression. In order to prevent Rb phosphorylation and cancer cell cycle progression, inhibitors of Cdk4 and Cdk6 have been developed in screens using a dimer of Cdk4 or Cdk6 and CycD due to technical challenges in generating the active form of p27 that can complex with Cdk4 or Cdk6 and CycD. However, the dimeric complex does not readily form in the cell. The protein p27 is always found together in complex with active Cdk4 or Cdk6 and CycD and may increase Cdk4/6-CycD stability. The disclosure features trimeric protein complexes comprising p27, Cdk4 (or a variant thereof) or Cdk6 (or a variant thereof), and CycD, in which the Cdk4 (or a variant thereof) or Cdk6 (or a variant thereof) in the trimeric protein complex is an active kinase. The trimeric protein complexes featured herein are closer mimics of the p27-Cdk4/6-CycD complexes found in vivo compared to the Cdk4/6-CycD dimeric complexes used in the past. The trimeric protein complexes described herein may serve as a better tool in screening and selecting chemical compounds that can function as inhibitors of the trimeric protein complex and Cdk4 or Cdk6 to prevent the phosphorylation of Rb, and accordingly, arresting cancer cell cycle progression.

In some embodiments, a trimeric protein complex described herein may comprise an engineered p27, a Cdk4 (or a variant thereof) or a Cdk6 (or a variant thereof), and a CycD (or a variant thereof), in which the Cdk4, Cdk6, or the variant thereof in the trimeric protein complex is an active kinase. The engineered p27 in the trimeric protein complex may have at least one amino acid substitution at a position selected from the group consisting of Y74, Y88, and Y89, in which the amino acid positions are determined with reference to the sequence of SEQ ID NO: 1. Examples of engineered p27 are provided in detail further herein.

In other embodiments, a trimeric protein complex may comprise a phosphorylated, wild-type p27, or a fragment thereof, a Cdk4 (or a variant thereof) or a Cdk6 (or a variant thereof), and a CycD (or a variant thereof), in which the Cdk4 (the variant thereof) or the Cdk6 (or the variant thereof) in the trimeric protein complex is an active kinase. In some embodiments, the phosphorylated, wild-type p27 or a fragment thereof comprises the sequence of any one of SEQ ID NOS: 1-3 and is phosphorylated at Y74, Y88, and/or Y89, wherein the amino acid positions are determined with reference to the sequence of SEQ ID NO: 1. In order to form a trimeric protein complex with an active Cdk4 (or a variant thereof) or Cdk6 (or a variant thereof), a wild-type p27 (or a fragment thereof) may be expressed from a separate cell line and phosphorylated by a kinase prior to formation of the trimeric protein complex.

IV. Engineered p27

The disclosure features an engineered p27 that can form a trimeric protein complex with a Cdk4 (or a variant thereof) or a Cdk6 (or a variant thereof), and a CycD (or a variant thereof). An engineered p27 as described herein may have at least one amino acid substitution at a position selected from the group consisting of Y74, Y88, and Y89, in which the amino acid positions are determined with reference to the sequence of SEQ ID NO: 1. In the trimeric protein complex, an engineered p27 may increase the stability of the dimer of Cdk4 (or a variant thereof) or Cdk6 (or a variant thereof) and CycD (or a variant thereof). In some embodiments, an engineered p27 may have the same length as a wild-type p27 and contains at least one amino acid substitution at a position selected from the group consisting of Y74, Y88, and Y89. In some embodiments, an engineered p27 may be a fragment of the wild-type p27 and contains at least one amino acid substitution at a position selected from the group consisting of Y74, Y88, and Y89.

In some embodiments, an engineered p27 may have one amino acid substitution at a position selected from the group consisting of Y74, Y88, and Y89. In some embodiments, an engineered p27 may have two amino acid substitutions at two positions selected from the group consisting of Y74, Y88, and Y89 (e.g., Y74 and Y88, Y74 and Y89, or Y88 and Y89). In some embodiments, an engineered p27 may have three amino acid substitutions at positions Y74, Y88, and Y89. In some embodiments, the amino acid substation at position Y74 may include, but are not limited to, Y74E and Y74D. In some embodiments, the amino acid substation at position Y74 may include, but are not limited to, Y74E, Y74D, and Y74R. The amino acid substitution at position Y88 may include, but are not limited to, Y88E and Y88D. The amino acid substitution at position Y89 may include, but are not limited to, Y89E and Y89D. In further embodiments, an engineered p27 may be phosphorylated, i.e., phosphorylated at a tyrosine residue (e.g., phosphorylated at one or more of Y74, Y88, and Y89).

Table 1 below lists the sequence of a wild-type p27, fragments of the wild-type p27, and various engineered p27 proteins containing at least one amino acid substitution at a position selected from the group consisting of Y74, Y88, and Y89, in which the amino acid positions are determined with reference to the sequence of SEQ ID NO: 1. An engineered p27 described herein may have at least 90% sequence identity (e.g., 92%, 93%, 94%, 95%, 96%, 97%, 98%, 99%, or 100%) to any one of the sequences of SEQ ID NOS: 1-36 listed in Table 1 and one or more amino acid substitutions, additions, and/or deletions relative to the wild-type p27 (SEQ ID NO: 1).

TABLE 1

| SEQ ID NO | Protein | Sequence |
|---|---|---|
| 1 | Full-length wild-type p27 | MSNVRVSNGSPSLERMDARQAEHPKPSACRNLFGPVDHEELTRDLE KHCRDMEEASQRKWNFDFQNHKPLEGKYEWQEVEKGSLPEFYYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 2 | Amino acids 25-106 of full-length wild-type p27 | KPSACRNLFGPVDHEELTRDLEKHCRDMEEASQRKWNFDFQNHKP LEGKYEWQEVEKGSLPEFYYRPPRPPKGACKVPAQES |
| 3 | Amino acids 25-98 of full-length wild-type p27 | KPSACRNLFGPVDHEELTRDLEKHCRDMEEASQRKWNFDFQNHKP LEGKYEWQEVEKGSLPEFYYRPPRPPKGA |
| 4 | Full-length p27 with Y74E | MSNVRVSNGSPSLERMDARQAEHPKPSACRNLFGPVDHEELTRDLE KHCRDMEEASQRKWNFDFQNHKPLEGKEEWQEVEKGSLPEFYYRP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |

TABLE 1-continued

| SEQ ID NO | Protein | Sequence |
|---|---|---|
| 5 | Amino acids 25-106 of p27 with Y74E | KPSACRNLFGPVDHEELTRDLEKHCRDMEEASQRKWNFDFQNHKP LEGKEEWQEVEKGSLPEFYYRPPRPPKGACKVPAQES |
| 6 | Amino acids 25-98 of p27 with Y74E | KPSACRNLFGPVDHEELTRDLEKHCRDMEEASQRKWNFDFQNHKP LEGKEEWQEVEKGSLPEFYYRPPRPPKGA |
| 7 | Full-length p27 with Y74D | MSNVRVSNGSPSLERMDARQAEHPKPSACRNLFGPVDHEELTRDLE KHCRDMEEASQRKWNFDFQNHKPLEGKDEWQEVEKGSLPEFYYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 8 | Amino acids 25-106 of p27 with Y74D | KPSACRNLFGPVDHEELTRDLEKHCRDMEEASQRKWNFDFQNHKP LEGKDEWQEVEKGSLPEFYYRPPRPPKGACKVPAQES |
| 9 | Amino acids 25-98 of p27 with Y74D | KPSACRNLFGPVDHEELTRDLEKHCRDMEEASQRKWNFDFQNHKP LEGKDEWQEVEKGSLPEFYYRPPRPPKGA |
| 10 | Full-length p27 with Y74R | MSNVRVSNGSPSLERMDARQAEHPKPSACRNLFGPVDHEELTRDLE KHCRDMEEASQRKWNFDFQNHKPLEGKREWQEVEKGSLPEFYYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 11 | Amino acids 25-106 of p27 with Y74R | KPSACRNLFGPVDHEELTRDLEKHCRDMEEASQRKWNFDFQNHKP LEGKREWQEVEKGSLPEFYYRPPRPPKGACKVPAQES |
| 12 | Amino acids of 25-98 p27 with Y74R | KPSACRNLFGPVDHEELTRDLEKHCRDMEEASQRKWNFDFQNHKP LEGKREWQEVEKGSLPEFYYRPPRPPKGA |
| 13 | Full-length p27 with Y88E | MSNVRVSNGSPSLERMDARQAEHPKPSACRNLFGPVDHEELTRDLE KHCRDMEEASQRKWNFDFQNHKPLEGKYEWQEVEKGSLPEFEYRP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 14 | Amino acids 25-106 of p27 with Y88E | KPSACRNLFGPVDHEELTRDLEKHCRDMEEASQRKWNFDFQNHKP LEGKYEWQEVEKGSLPEFEYRPPRPPKGACKVPAQES |
| 15 | Amino acids 25-98 of p27 with Y88E | KPSACRNLFGPVDHEELTRDLEKHCRDMEEASQRKWNFDFQNHKP LEGKYEWQEVEKGSLPEFEYRPPRPPKGA |
| 16 | Full-length p27 with Y88D | MSNVRVSNGSPSLERMDARQAEHPKPSACRNLFGPVDHEELTRDLE KHCRDMEEASQRKWNFDFQNHKPLEGKYEWQEVEKGSLPEFDYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 17 | Amino acids 25-106 of p27 with Y88D | KPSACRNLFGPVDHEELTRDLEKHCRDMEEASQRKWNFDFQNHKP LEGKYEWQEVEKGSLPEFDYRPPRPPKGACKVPAQES |
| 18 | Amino acids 25-98 of p27 with Y88D | KPSACRNLFGPVDHEELTRDLEKHCRDMEEASQRKWNFDFQNHKP LEGKYEWQEVEKGSLPEFDYRPPRPPKGA |
| 19 | Full-length p27 with Y89E | MSNVRVSNGSPSLERMDARQAEHPKPSACRNLFGPVDHEELTRDLE KHCRDMEEASQRKWNFDFQNHKPLEGKYEWQEVEKGSLPEFYERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 20 | Amino acids 25-106 of p27 with Y89E | KPSACRNLFGPVDHEELTRDLEKHCRDMEEASQRKWNFDFQNHKP LEGKYEWQEVEKGSLPEFYERPPRPPKGACKVPAQES |
| 21 | Amino acids 25-98 of p27 with Y89E | KPSACRNLFGPVDHEELTRDLEKHCRDMEEASQRKWNFDFQNHKP LEGKYEWQEVEKGSLPEFYERPPRPPKGA |

TABLE 1-continued

| SEQ ID NO | Protein | Sequence |
|---|---|---|
| 22 | Full-length p27 with Y89D | MSNVRVSNGSPSLERMDARQAEHPKPSACRNLFGPVDHEELTRDLE KHCRDMEEASQRKWNFDFQNHKPLEGKYEWQEVEKGSLPEFYDR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 23 | Amino acids 25-106 of p27 with Y89D | KPSACRNLFGPVDHEELTRDLEKHCRDMEEASQRKWNFDFQNHKP LEGKYEWQEVEKGSLPEFYDRPPRPPKGACKVPAQES |
| 24 | Amino acids of p27 25-98 with Y89D | KPSACRNLFGPVDHEELTRDLEKHCRDMEEASQRKWNFDFQNHKP LEGKYEWQEVEKGSLPEFYDRPPRPPKGA |
| 25 | Full length-p27 with Y74E and Y88E | MSNVRVSNGSPSLERMDARQAEHPKPSACRNLFGPVDHEELTRDLE KHCRDMEEASQRKWNFDFQNHKPLEGKEEWQEVEKGSLPEFYRP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 26 | Amino acids 25-106 of p27 with Y74E and Y88E | KPSACRNLFGPVDHEELTRDLEKHCRDMEEASQRKWNFDFQNHKP LEGKEEWQEVEKGSLPEFEYRPPRPPKGACKVPAQES |
| 27 | Amino acids 25-98 of p27 with Y74E and Y88E | KPSACRNLFGPVDHEELTRDLEKHCRDMEEASQRKWNFDFQNHKP LEGKEEWQEVEKGSLPEFEYRPPRPPKGA |
| 28 | Full-length p27 with Y74E and Y89E | MSNVRVSNGSPSLERMDARQAEHPKPSACRNLFGPVDHEELTRDLE KHCRDMEEASQRKWNFDFQNHKPLEGKEEWQEVEKGSLPEFYERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 29 | Amino acids 25-106 of p27 with Y74E and Y89E | KPSACRNLFGPVDHEELTRDLEKHCRDMEEASQRKWNFDFQNHKP LEGKEEWQEVEKGSLPEFYERPPRPPKGACKVPAQES |
| 30 | Amino acids 25-98 of p27 with Y74E and Y89E | KPSACRNLFGPVDHEELTRDLEKHCRDMEEASQRKWNFDFQNHKP LEGKEEWQEVEKGSLPEFYERPPRPPKGA |
| 31 | Full-length p27 with Y88E and Y89E | MSNVRVSNGSPSLERMDARQAEHPKPSACRNLFGPVDHEELTRDLE KHCRDMEEASQRKWNFDFQNHKPLEGKYEWQEVEKGSLPEFEERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 32 | Amino acids 25-106 of p27 with Y88E and Y89E | KPSACRNLFGPVDHEELTRDLEKHCRDMEEASQRKWNFDFQNHKP LEGKYEWQEVEKGSLPEFEERPPRPPKGACKVPAQES |
| 33 | Amino acids 25-98 of p27 with Y88E and Y89E | KPSACRNLFGPVDHEELTRDLEKHCRDMEEASQRKWNFDFQNHKP LEGKYEWQEVEKGSLPEFEERPPRPPKGA |
| 34 | Full-length p27 with Y74E, Y88E, and Y89E | MSNVRVSNGSPSLERMDARQAEHPKPSACRNLFGPVDHEELTRDLE KHCRDMEEASQRKWNFDFQNHKPLEGKEEWQEVEKGSLPEFEERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 35 | Amino acids 25-106 of p27 with Y74E, Y88E, and Y89E | KPSACRNLFGPVDHEELTRDLEKHCRDMEEASQRKWNFDFQNHKP LEGKEEWQEVEKGSLPEFEERPPRPPKGACKVPAQES |

TABLE 1-continued

| SEQ ID NO | Protein | Sequence |
|---|---|---|
| 36 | Amino acids 25-98 of p27 with Y74E, Y88E, and Y89E | KPSACRNLFGPVDHEELTRDLEKHCRDMEEASQRKWNFDFQNHKP LEGKEEWQEVEKGSLPEFEERPPRPPKGA |

V. Cdk4, Cdk6, or a Variant Thereof

Cyclin-dependent kinase 4 or 6 (Cdk4 or Cdk6), when in complex with p27 and CycD, may act as an active kinase in phosphorylating Rb. The Cdk4 or Cdk6 in the trimeric protein complexes described herein may be a wild-type Cdk4 or a wild-type Cdk6, respectively. In other embodiments, the Cdk4 or Cdk6 in the trimeric protein complexes described herein may be a variant of the wild-type Cdk4 or the wild-type Cdk6, respectively, containing one or more amino acid substitutions, additions, and/or deletions relative to the wild-type protein sequence. A Cdk4 or Cdk6 variant may have the same length as the wild-type protein or may be a fragment of the wild-type protein. A Cdk4 variant or Cdk6 variant described herein is capable of phosphorylation activity and can form a trimeric complex with a CycD or a variant thereof, and an engineered p27.

Table 2 below lists the sequences of wild-type Cdk4 and Cdk6 and various Cdk4 and Cdk6 variants containing one or more amino acid substitutions relative to the wild-type protein, in which the amino acid positions are determined with reference to the sequence of SEQ ID NO: 37 (Cdk4) or SEQ ID NO: 52 (Cdk6). A Cdk4 variant described herein may have at least 90% sequence identity (e.g., 92%, 93%, 94%, 95%, 96%, 97%, 98%, 99%, or 100%) to any one of the sequences of SEQ ID NOS: 37-51 listed in Table 2 and one or more amino acid substitutions, additions, and/or deletions relative to the wild-type Cdk4 (SEQ ID NO: 37). A Cdk6 variant described herein may have at least 90% sequence identity (e.g., 92%, 93%, 94%, 95%, 96%, 97%, 98%, 99%, or 100%) to any one of the sequences of SEQ ID NOS: 52-54 listed in Table 2 and one or more amino acid substitutions, additions, and/or deletions relative to the wild-type Cdk4 (SEQ ID NO: 52).

TABLE 2

| SEQ ID NO | Protein | Sequence |
|---|---|---|
| 37 | Wild-type Cdk4 | MATSRYEPVAEIGVGAYGTVYKARDPHSGHFVALKSVRVPNGGGG GGGLPISTVREVALLRRLEAFEHPNVVRLMDVCATSRTDREIKVTL VFEHVDQDLRTYLDKAPPPGLPAETIKDLMRQFLRGLDFLHANCIV HRDLKPENILVTSGGTVKLADFGLARIYSYQMALTPVVVTLWYRAP EVLLQSTYATPVDMWSVGCIFAEMFRRKPLFCGNSEADQLGKIFDL IGLPPEDDWPRDVSLPRGAFPPRGPRPVQSVVPEMEESGAQLLLEM LTFNPHKRISAFRALQHSYLHKDEGNPE |
| 38 | Cdk4 variant with T172D | MATSRYEPVAEIGVGAYGTVYKARDPHSGHFVALKSVRVPNGGGG GGGLPISTVREVALLRRLEAFEHPNVVRLMDVCATSRTDREIKVTL VFEHVDQDLRTYLDKAPPPGLPAETIKDLMRQFLRGLDFLHANCIV HRDLKPENILVTSGGTVKLADFGLARIYSYQMALDPVVVTLWYRA PEVLLQSTYATPVDMWSVGCIFAEMFRRKPLFCGNSEADQLGKIFD LIGLPPEDDWPRDVSLPRGAFPPRGPRPVQSVVPEMEESGAQLLLE MLTFNPHKRISAFRALQHSYLHKDEGNPE |
| 39 | Cdk4 variant with T172E | MATSRYEPVAEIGVGAYGTVYKARDPHSGHFVALKSVRVPNGGGG GGGLPISTVREVALLRRLEAFEHPNVVRLMDVCATSRTDREIKVTL VFEHVDQDLRTYLDKAPPPGLPAETIKDLMRQFLRGLDFLHANCIV HRDLKPENILVTSGGTVKLADFGLARIYSYQMALEPVVVTLWYRAP EVLLQSTYATPVDMWSVGCIFAEMFRRKPLFCGNSEADQLGKIFDL IGLPPEDDWPRDVSLPRGAFPPRGPRPVQSVVPEMEESGAQLLLEM LTFNPHKRISAFRALQHSYLHKDEGNPE |
| 40 | Cdk4 variant with amino acids 44 to 46 deleted, G43E, and G47E | MATSRYEPVAEIGVGAYGTVYKARDPHSGHFVALKSVRVPNGEEG LPISTVREVALLRRLEAFEHPNVVRLMDVCATSRTDREIKVTLVFEH VDQDLRTYLDKAPPPGLPAETIKDLMRQFLRGLDFLHANCIVHRDL KPENILVTSGGTVKLADFGLARIYSYQMALTPVVVTLWYRAPEVLL QSTYATPVDMWSVGCIFAEMFRRKPLFCGNSEADQLGKIFDLIGLPP EDDWPRDVSLPRGAFPPRGPRPVQSVVPEMEESGAQLLLEMLTFNP HKRISAFRALQHSYLHKDEGNPE |
| 41 | Cdk4 variant with amino acids 44 to 46 deleted, G43D, and G47E | MATSRYEPVAEIGVGAYGTVYKARDPHSGHFVALKSVRVPNGDEG LPISTVREVALLRRLEAFEHPNVVRLMDVCATSRTDREIKVTLVFEH VDQDLRTYLDKAPPPGLPAETIKDLMRQFLRGLDFLHANCIVHRDL KPENILVTSGGTVKLADFGLARIYSYQMALTPVVVTLWYRAPEVLL QSTYATPVDMWSVGCIFAEMFRRKPLFCGNSEADQLGKIFDLIGLPP EDDWPRDVSLPRGAFPPRGPRPVQSVVPEMEESGAQLLLEMLTFNP HKRISAFRALQHSYLHKDEGNPE |

TABLE 2-continued

| SEQ ID NO | Protein | Sequence |
|---|---|---|
| 42 | Cdk4 variant with amino acids 44 to 46 deleted, G43E, and G47D | MATSRYEPVAEIGVGAYGTVYKARDPHSGHFVALKSVRVPNGEDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALTPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 43 | Cdk4 variant with amino acids 44 to 46 deleted, G43D, and G47D | MATSRYEPVAEIGVGAYGTVYKARDPHSGHFVALKSVRVPNGDDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALTPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 44 | Cdk4 variant with T172D, amino acids 44 to 46 deleted, G43E, and G47E | MATSRYEPVAEIGVGAYGTVYKARDPHSGHFVALKSVRVPNGEEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 45 | Cdk4 variant with T172D, amino acids 44 to 46 deleted, G43D, and G47E | MATSRYEPVAEIGVGAYGTVYKARDPHSGHFVALKSVRVPNGDEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 46 | Cdk4 variant with T172D, amino acids 44 to 46 deleted, G43E, and G47D | MATSRYEPVAEIGVGAYGTVYKARDPHSGHFVALKSVRVPNGEDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 47 | Cdk4 variant with T172D, amino acids 44 to 46 deleted, G43D, and G47D | MATSRYEPVAEIGVGAYGTVYKARDPHSGHFVALKSVRVPNGDDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 48 | Cdk4 variant with T172E, amino acids 44 to 46 deleted, G43E, and G47E | MATSRYEPVAEIGVGAYGTVYKARDPHSGHFVALKSVRVPNGEEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALEPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 49 | Cdk4 variant with T172E, amino acids 44 to 46 deleted, G43D, and G47E | MATSRYEPVAEIGVGAYGTVYKARDPHSGHFVALKSVRVPNGDEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALEPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 50 | Cdk4 variant with T172E, amino acids 44 to 46 deleted, G43E, and G47D | MATSRYEPVAEIGVGAYGTVYKARDPHSGHFVALKSVRVPNGEDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALEPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 51 | Cdk4 variant with T172E, amino acids | MATSRYEPVAEIGVGAYGTVYKARDPHSGHFVALKSVRVPNGDDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL |

TABLE 2-continued

| SEQ ID NO | Protein | Sequence |
|---|---|---|
| | 44 to 46 deleted, G43D, and G47D | KPENILVTSGGTVKLADFGLARIYSYQMALEPVVVTLWYRAPEVLL QSTYATPVDMWSVGCIFAEMFRRKPLFCGNSEADQLGKIFDLIGLPP EDDWPRDVSLPRGAFPPRGPRPVQSVVPEMEESGAQLLLEMLTFNP HKRISAFRALQHSYLHKDEGNPE |
| 52 | Wild-type Cdk6 | MEKDGLCRADQQYECVAEIGEGAYGKVFKARDLKNGGRFVALKR VRVQTGEEGMPLSTIREVAVLRHLETFEHPNVVRLFDVCTVSRTDR ETKLTLVFEHVDQDLTTYLDKVPEPGVPTETIKDMMFQLLRGLDFL HSHRVVHRDLKPQNILVTSSGQIKLADFGLARIYSFQMALTSVVVTL WYRAPEVLLQSSYATPVDLWSVGCIFAEMFRRKPLFRGSSDVDQLG KILDVIGLPGEEDWPRDVALPRQAFHSKSAQPIEKFVTDIDELGKDL LLKCLTFNPAKRISAYSALSHPYFQDLERCKENLDSHLPPSQNTSEL NTA |
| 53 | Cdk6 variant with T177D | MEKDGLCRADQQYECVAEIGEGAYGKVFKARDLKNGGRFVALKR VRVQTGEEGMPLSTIREVAVLRHLETFEHPNVVRLFDVCTVSRTDR ETKLTLVFEHVDQDLTTYLDKVPEPGVPTETIKDMMFQLLRGLDFL HSHRVVHRDLKPQNILVTSSGQIKLADFGLARIYSFQMALDSVVVT LWYRAPEVLLQSSYATPVDLWSVGCIFAEMFRRKPLFRGSSDVDQL GKILDVIGLPGEEDWPRDVALPRQAFHSKSAQPIEKFVTDIDELGKD LLLKCLTFNPAKRISAYSALSHPYFQDLERCKENLDSHLPPSQNTSE LNTA |
| 54 | Cdk6 variant with T177E | MEKDGLCRADQQYECVAEIGEGAYGKVFKARDLKNGGRFVALKR VRVQTGEEGMPLSTIREVAVLRHLETFEHPNVVRLFDVCTVSRTDR ETKLTLVFEHVDQDLTTYLDKVPEPGVPTETIKDMMFQLLRGLDFL HSHRVVHRDLKPQNILVTSSGQIKLADFGLARIYSFQMALESVVVTL WYRAPEVLLQSSYATPVDLWSVGCIFAEMFRRKPLFRGSSDVDQLG KILDVIGLPGEEDWPRDVALPRQAFHSKSAQPIEKFVTDIDELGKDL LLKCLTFNPAKRISAYSALSHPYFQDLERCKENLDSHLPPSQNTSEL NTA |

VI. Cyclin D

The CycD or a variant thereof in the trimeric protein complexes described herein may be a wild-type CycD or a variant of the wild-type CycD. A wild-type CycD may be a wild-type CycD1, CycD2, or CycD3. A CycD variant comprises one or more amino acid substitutions, additions, and/or deletions relative to the wild-type protein sequence (e.g., wild-type CycD1, CycD2, or CycD3). A trimeric protein complex comprising an active Cdk4 (or a variant thereof) or Cdk6 (or a variant thereof) describe herein may comprise any one of CycD1, CycD2, CycD3, or a variant thereof described herein.

Table 3 below lists the sequences of wild-type CycD1, CycD2, CycD3, and various CycD variants containing one or more amino acid substitutions relative to the wild-type protein, in which the amino acid positions are determined with reference to the sequence of SEQ ID NO: 55 (CycD), SEQ ID NO: 57 (CycD2), or SEQ ID NO: 58 (CycD3). A CycD1 variant described herein may have at least 90% sequence identity (e.g., 92%, 93%, 94%, 95%, 96%, 97%, 98%, 99%, or 100%) to the sequence of SEQ ID NO: 55 or 56 listed in Table 3 and one or more amino acid substitutions, additions, and/or deletions relative to the wild-type CycD1 (SEQ ID NO: 55). A CycD2 variant described herein may have at least 90% sequence identity (e.g., 92%, 93%, 94%, 95%, 96%, 97%, 98%, 99%, or 100%) to the sequence of SEQ ID NO: 57 listed in Table 3 and one or more amino acid substitutions, additions, and/or deletions relative to the wild-type CycD2 (SEQ ID NO: 57). A CycD3 variant described herein may have at least 90% sequence identity (e.g., 92%, 93%, 94%, 95%, 96%, 97%, 98%, 99%, or 100%) to the sequence of SEQ ID NO: 58 listed in Table 3 and one or more amino acid substitutions, additions, and/or deletions relative to the wild-type CycD3 (SEQ ID NO: 58).

TABLE 3

| SEQ ID NO | Protein | Sequence |
|---|---|---|
| 55 | Full-length wild-type CycD1 | MEHQLLCCEVETIRRAYPDANLLNDRVLRAMLKAEETCAPSVSYF KCVQKEVLPSMRKIVATWMLEVCEEQKCEEEVFPLAMNYLDRFLS LEPVKKSRLQLLGATCMFVASKMKETIPLTAEKLCIYTDNSIRPEEL LQMELLLVNKLKWNLAAMTPHDFIEHFLSKMPEAEENKQIIRKHAQ TFVALCATDVKFISNPPSMVAAGSVVAAVQGLNLRSPNNFLSYYRL TRFLSRVIKCDPDCLRACQEQIEALLESSLRQAQQNMDPKAAEEEEE EEEEVDLACTPTDVRDVDI |
| 56 | Amino acids 19-267 of full-length wild-type CycD1 | DANLLNDRVLRAMLKAEETCAPSVSYFKCVQKEVLPSMRKIVATW MLEVCEEQKCEEEVFPLAMNYLDRFLSLEPVKKSRLQLLGATCMF VASKMKETIPLTAEKLCIYTDNSIRPEELLQMELLLVNKLKWNLAA MTPHDFIEHFLSKMPEAEENKQIIRKHAQTFVALCATDVKFISNPPS MVAAGSVVAAVQGLNLRSPNNFLSYYRLTRFLSRVIKCDPDCLRAC QEQIEALLESSLRQAQQNMD |

TABLE 3-continued

| SEQ ID NO | Protein | Sequence |
|---|---|---|
| 57 | Full-length wild-type CycD2 | MELLCHEVDPVRRAVRDRNLLRDDRVLQNLLTIEERYLPQCSYFKC VQKDIQPYMRRMVATWMLEVCEEQKCEEEVFPLAMNYLDRFLAG VPTPKSHLQLLGAVCMFLASKLKETSPLTAEKLCIYTDNSIKPQELL EWELVVLGKLKWNLAAVTPHDFIEHILRKLPQQREKLSLIRKHAQT FIALCATDFKFAMYPPSMIATGSVGAAICGLQQDEEVSSLTCDALTE LLAKITNTDVDCLKACQEQIEAVLLNSLQQYRQDQRDGSKSEDELD QASTPTDVRDIDL |
| 58 | Full-length wild-type CycD3 | MELLCCEGTRHAPRAGPDPRLLGDQRVLQSLLRLEERYVPRASYFQ CVQREIKPHMRKMLAYWMLEVCEEQRCEEEVFPLAMNYLDRYLS CVPTRKAQLQLLGAVCMLLASKLRETTPLTIEKLCIYTDHAVSPRQL RDWEVLVLGKLKWDLAAVIAHDFLAFILHRLSLPRDRQALVKKHA QTFLALCATDYTFAMYPPSMIATGSIGAAVQGLGACSMSGDELTEL LAGITGTEVDCLRACQEQIEAALRESLREASQTSSSPAPKAPRGSSSQ GPSQTSTPTDVTAIHL |

VI. Methods of Generating a Trimeric Protein Complex

In some embodiments, for a trimeric protein complex comprising an engineered p27, a Cdk4 (or a variant thereof) or a Cdk6 (or a variant thereof), and a CycD (or a variant thereof), each member of the trimeric protein complex may be expressed from the same cell line or from separate cell lines. In some embodiments, all three members may be co-expressed from the same cell line, in which each member may be encoded in an expression vector configured to express the protein. In other embodiments, for a trimeric protein complex comprising a phosphorylated, wild-type p27 or a fragment thereof (e.g., any one of SEQ ID NOS: 1-3), a Cdk4 (or a variant thereof) or a Cdk6 (or a variant thereof), and a CycD (or a variant thereof), the wild-type p27, or a fragment thereof, may be expressed in a cell line separately from the other two members of the complex. Once the wild-type p27, or a fragment thereof, is isolated and purified, the wild-type p27, or a fragment thereof, may be incubated with a kinase (e.g., Brk kinase, Src kinase, and Abl kinase) in order to generate the phosphorylated wild-type p27 or fragment thereof. The phosphorylated, wild-type p27, or fragment thereof, may then be incubated with the Cdk4 (or a variant thereof) or Cdk6 (or a variant thereof), and the CycD or a variant thereof, in order to generate the trimeric protein complex.

Each protein in the trimeric protein complex described herein may be produced from a host cell. A host cell refers to a vehicle that includes the necessary cellular components, e.g., organelles, needed to express the proteins and complexes described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc.). The choice of nucleic acid vectors depends in part on the host cells to be used. Generally, preferred host cells are of either prokaryotic (e.g., bacterial) or eukaryotic (e.g., insect or mammalian) origin.

Nucleic Acid Vectors and Host Cells

A nucleic acid sequence encoding the amino acid sequence of a protein (e.g., a engineered p27) may be prepared by a variety of methods known in the art. These methods include, but are not limited to, oligonucleotide-mediated (or site-directed) mutagenesis and PCR mutagenesis. A nucleic acid molecule encoding a protein may be obtained using standard techniques, e.g., gene synthesis. Alternatively, a nucleic acid molecule encoding a wild-type protein (e.g., a wild-type p27 having the sequence of SEQ ID NO: 1) may be mutated to contain specific amino acid substitutions using standard techniques in the art, e.g., QuikChange™ mutagenesis. Nucleic acid molecules may be synthesized using a nucleotide synthesizer or PCR techniques.

Nucleic acid sequences encoding a protein in the trimeric protein complex of the disclosure (e.g., an engineered p27) may be inserted into a vector capable of replicating and expressing the nucleic acid molecules in prokaryotic or eukaryotic host cells. Many vectors are available in the art and can be used for the purpose of the disclosure. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding the protein of interest, and a transcription termination sequence. In some embodiments, a vector used to express a protein in the trimeric protein complex may be a baculovirus vector. In some embodiments, the baculovirus vector may have a polyhedrin promoter. In some embodiments, a vector used to express a protein in the trimeric protein complex may be a PGEX vector. In some embodiments, the PGEX vector may have a T7 promoter.

In some embodiments, insect cells are used as host cells for the disclosure. Examples of insect cells types include, but are not limited to, Sf9, Sf21, and S2 cells. In particular embodiments, Sf9 cells may be used to express a protein in the trimeric protein complex of the disclosure. In other embodiments, E. coli cells are used as host cells for the invention. Examples of E. coli strains include, but are not limited to, E. coli 294 (ATCC® 31,446), E. coli k 1776 (ATCC® 31,537, E. coli BL21 (DE3) (ATCC® BAA-1025), and E. coli RV308 (ATCC® 31,608). Different host cells have characteristic and specific mechanisms for the post-translational processing and modification of protein products. In other embodiments, mammalian cells are used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NSO, Sp2/0, VERY, BHK, MDCK, W138, BT483, Hs578T, HTB2, BT20, T47D, NSO (a murine myeloma cell line that does not endogenously produce any immunoglobulin chains), CRL7030, and HsS78Bst cells. Appropriate cell lines or host systems may be chosen to ensure the correct modification and processing of the protein expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) Recombinant Gene Expression: Reviews and Protocols (*Methods in Molecular Biology*), Humana Press; 2nd ed. 2004 (Jul. 20, 2004) and Vladimir Voynov and Justin A. Caravella (eds.) Therapeutic Proteins: Methods and Protocols (*Methods in Molecular Biology*) Humana Press; 2nd ed. 2012 (Jun. 28, 2012).

Protein Production, Recovery, and Purification

Host cells used to produce the proteins and complexes of the disclosure may be grown in media known in the art and suitable for culturing of the selected host cells. Examples of suitable media for bacterial host cells include Luria broth (LB) plus necessary supplements, such as a selection agent, e.g., ampicillin. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Host cells are cultured at suitable temperatures, such as from about 20° C. to about 39° C., e.g., from 25° C. to about 37° C., preferably 37° C., and $CO_2$ levels, such as 5 to 10% (preferably 8%). The pH of the medium is generally from about 6.8 to 7.4, e.g., 7.0, depending mainly on the host organism. If an inducible promoter is used in the expression vector of the invention, protein expression may be induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified. A protein or complex of the disclosure may be purified by any method known in the art of protein purification, for example, by protein A affinity, other chromatography (e.g., ion exchange, affinity, and size-exclusion column chromatography), centrifugation, differential solubility, or by any other standard technique for the purification of proteins. (see Process Scale Purification of Antibodies, Uwe Gottschalk (ed.) John Wiley & Sons, Inc., 2009).

In some instances, a protein may be conjugated to a purification tag to facilitate purification and isolation of the protein from, e.g., a whole cell lysate mixture. In some embodiments, the purification tag binds to another moiety that has a specific affinity for the purification tag. In some embodiments, such moieties which specifically bind to the purification tag are attached to a solid support, such as a matrix, a resin, or agarose beads. Examples of purification tags that may be joined to a protein include, but are not limited to, a glutathione S-transferase (GST) tag and a hexa-histidine peptide (SEQ ID NO: 66). GST is a 211 amino acid protein (about 26 kDa) whose DNA sequence may be integrated into expression vectors for production of recombinant proteins. The result of expression from this vector is a GST-tagged fusion protein in which the functional GST protein may be fused to, e.g., the N-terminus or C-terminus of the recombinant protein. Because GST folds rapidly into a stable and highly soluble protein upon translation, inclusion of the GST tag may promote greater expression and solubility of recombinant proteins than expression without the tag. In addition, GST-tagged fusion proteins may be purified or detected based on the ability of GST to bind its substrate, glutathione (GSH). In some embodiments, a solid support may be functionalized with GSH to isolate and purified GST-tagged fusion proteins. A hexa-histidine peptide (HHHHHH (SEQ ID NO: 66)) binds to nickel-functionalized agarose affinity column with micromolar affinity. In some embodiments, the purification tag may be cleaved from the fusion protein once it is purified. A protease cleavage sequence (e.g., a TEV protease cleavage sequence ENLYFQG (SEQ ID NO: 67) may be inserted between the protein of interest and the purification tag.

In other embodiments, a FLAG peptide, a myc peptide, or a hemagglutinin (HA) peptide may be used as a purification tag. In some embodiments, a FLAG peptide includes the sequence DYKDDDDK (SEQ ID NO: 68). In some embodiments, a FLAG peptide includes integer multiples of the sequence DYKDDDDK (SEQ ID NO: 68) in tandem series, e.g., 3×DYKDDDDK (SEQ ID NO: 71). In some embodiments, a myc peptide includes the sequence EQKLISEEDL (SEQ ID NO: 69). In some embodiments, a myc peptide includes integer multiples of the sequence EQKLISEEDL (SEQ ID NO: 69) in tandem series, e.g., 3×EQKLISEEDL (SEQ ID NO: 72). In some embodiments, an HA peptide includes the sequence YPYDVPDYA (SEQ ID NO: 70). In some embodiments, an HA peptide includes integer multiples of the sequence YPYDVPDYA (SEQ ID NO: 70) in tandem series, e.g., 3×YPYDVPDYA (SEQ ID NO: 73). Antibodies that specifically recognize and bind to the FLAG, myc, or HA purification tag are well-known in the art and often commercially available. A solid support (e.g., a matrix, a resin, or agarose beads) functionalized with these antibodies may be used to purify a protein that includes a FLAG, myc, or HA peptide.

VIII. Methods of Screening Inhibitors

The disclosure also features methods of screening for inhibitors of the trimeric protein complexes described herein, which are closer mimics of the p27-Cdk4/6-CycD complexes found in vivo compared to the Cdk4/6-CycD dimeric complexes. The method comprises (a) providing the trimeric protein complex by incubating: (i) an engineered p27 described herein or a phosphorylated, wild-type p27 or a fragment thereof (e.g., any one of SEQ ID NOS: 1-36); (ii) a Cdk4 (or a variant thereof) or Cdk6 (or a variant thereof); and (iii) a CycD or a variant thereof, under conditions that allow the formation of the trimeric protein complex comprising an active Cdk4 (or a variant thereof) or Cdk6 (or a variant thereof); (b) contacting the trimeric protein complex with a compound and a substrate of the Cdk4 (or a variant thereof) or Cdk6 (or a variant thereof); (c) determining the phosphorylation status of the substrate, wherein the compound is an inhibitor of the trimeric protein complex if the compound inhibits the phosphorylation activity of the Cdk4 (or a variant thereof) or Cdk6 (or a variant thereof).

In some embodiments of the methods of screening for inhibitors of the trimeric protein complexes described herein, the substrate used may comprise a phosphorylation site having the sequence is $X_1PX_2X_3$ (SEQ ID NO: 60), wherein $X_1$ is S or T; $X_2$ is any amino acid; and $X_3$ is K or R. An active Cdk4 (or a variant thereof) or Cdk6 (or a variant thereof) in the complex may phosphorylate the substrate at $X_1$ in the phosphorylation site. In some embodiments, any protein having a phosphorylation site having the sequence is X₁PX₂X₃ (SEQ ID NO: 60) may be used in the methods. Examples of a substrate include, but are not limited to, Rb, FoxM1, histone H1, or a variant thereof. The sequences of some exemplary substrates and their variants are listed in Table 4 below.

ment of reactivity of the phosphorylated protein with a labeled phospho-threonine specific antibody. Antibodies specific for certain phosphorylated threonine residues may also be used directly on live cells with phosphorylated proteins on the cell surface or on whole cell lysates or a mixture of proteins after the lysates or the mixture of

TABLE 4

| SEQ ID NO | Protein | Sequence |
|---|---|---|
| 61 | Full-length, wild-type Rb | MPPKTPRKTAATAAAAAAEPPAPPPPPPPEEDPEQDSGPEDLPLVR LEFEETEEPDFTALCQKLKIPDHVRERAWLTWEKVSSVDGVLGGY IQKKKELWGICIFIAAVDLDEMSFTFTELQKNIEISVHKFFNLLKEI DTSTKVDNAMSRLLKKYDVLFALFSKLERTCELIYLTQPSSSISTEI NSALVLKVSWITFLLAKGEVLQMEDDLVISFQLMLCVLDYFIKLS PPMLLKEPYKTAVIPINGSPRTPRRGQNRSARIAKQLENDTRIIEVL CKEHECNIDEVKNVYFKNFIPFMNSLGLVTSNGLPEVENLSKRYE EIYLKNKDLDARLFLDHDKTLQTDSIDSFETQRTPRKSNLDEEVNV IPPHTPVRTVMNTIQQLMMILNSASDQPSENLISYFNNCTVNPKESI LKRVKDIGYIFKEKFAKAVGQGCVEIGSQRYKLGVRLYYRVMES MLKSEEERLSIQNFSKLLNDNIFHMSLLACALEVVMATYSRSTSQ NLDSGTDLSFPWILNVLNLKAFDFYKVIESFIKAEGNLTREMIKHL ERCEHRIMESLAWLSDSPLFDLIKQSKDREGPTDHLESACPLNLPL QNNHTAADMYLSPVRSPKKKGSTTRVNSTANAETQATSAFQTQK PLKSTSLSLFYKKVYRLAYLRLNTLCERLLSEHPELEHIIWTLFQHT LQNEYELMRDRHLDQIMMCSMYGICKVKNIDLKFKIIVTAYKDLP HAVQETFKRVLIKEEEYDSIIVFYNSVFMQRLKTNILQYASTRPPTL SPIPHIPRSPYKFPSSPLRIPGGNIYISPLKSPYKISEGLPTPTKMTPRS RILVSIGESFGTSEKFQKINQMVCNSDRVLKRSAEGSNPPKPLKKL RFDIEGSDEADGSKHLPGESKFQQKLAEMTSTRTRMQKQKMNDS MDTSNKEEK |
| 62 | C-terminal fragment (amino acids 771-928) of wild-type Rb | YASTRPPTLSPIPHIPRSPYKFPSSPLRIPGGNIYISPLKSPYKISEGLP TPTKMTPRSRILVSIGESFGTSEKFQKINQMVCNSDRVLKRSAEGS NPPKPLKKLRFDIEGSDEADGSKHLPGESKFQQKLAEMTSTRTRM QKQKMNDSMDTSNKEEK |
| 63 | Full-length, wild-type FoxM1 | MKTSPRRPLILKRRRLPLPVQNAPSETSEEEPKRSPAQQESNQAEA SKEVAESNSCKFPAGIKIINHPTMPNTQVVAIPNNANIHSIITALTA KGKESGSSGPNKFILISCGGAPTQPPGLRPQTQTSYDAKRTEVTLE TLGPKPAARDVNLPRPPGALCEQKRETCADGEAAGCTINNSLSNI QWLRKMSSDGLGSRSIKQEMEEKENCHLEQRQVKVEEPSRPSAS WQNSVSERPPYSYMAMIQFAINSTERKRMTLKDIYTWIEDHFPYF KHIAKPGWKNSIRHNLSLHDMFVRETSANGKVSFWTIHPSANRYL TLDQVFKPLDPGSPQLPEHLESQQKRPNPELRRNMTIKTELPLGAR RKMKPLLPRVSSYLVPIQFPVNQSLVLQPSVKVPLPLAASLMSSEL ARHSKRVRIAPKVLLAEEGIAPLSSAGPGKEEKLLFGEGFSPLLPV QTIKEEEIQPGEEMPHLARPIKVESPPLEEWPSPAPSFKEESSHSWE DSSQSPTPRPKKSYSGLRSPTRCVSEMLVIQHRERRERSRSRRKQH LLPPCVDEPELLFSEGPSTSRWAAELPFPADSSDPASQLSYSQEVG GPFKTPIKETLPISSTPSKSVLPRTPESWRLTPPAKVGGLDFSPVQTS QGASDPLPDPLGLMDLSTTPLQSAPPLESPQRLLSSEPLDLISVPFG NSSPSDIDVPKPGSPEPQVSGLAANRSLTEGLVLDTMNDSLSKILL DISFPGLDEDPLGPDNINWSQFIPELQ |
| 64 | Transactivation domain (amino acids 526-748) of wild-type FoxM1 | CVSEMLVIQHRERRERSRSRRKQHLLPPCVDEPELLFSEGPSTSRW AAELPFPADSSDPASQLSYSQEVGGPFKTPIKETLPISSTPSKSVLPR TPESWRLTPPAKVGGLDFSPVQTSQGASDPLPDPLGLMDLSTTPL QSAPPLESPQRLLSSEPLDLISVPFGNSSPSDIDVPKPGSPEPQVSGL AANRSLTEGLVLDTMNDSLSKILLDISFPGLDEDPL |
| 65 | Full-length, wild-type histone H1 | MSETVPPAPAASAAPEKPLAGKKAKKPAKAAAASKKKPAGPSVS ELIVQAASSSKERGGVSLAALKKALAAAGYDVEKNNSRIKLGIKS LVSKGTLVQTKGTGASGSFKLNKKASSVETKPGASKVATKTKAT GASKKLKKATGASKKSVKTPKKAKKPAATRKSSKNPKKPKTVKP KKVAKSPAKAKAVKPKAAKARVTKPKTAKPKKAAPKKK |

Methods and techniques for determining the phosphorylation status of a protein are available in the art. For example, radioactive $^{32}$P-ATP may be used in phosphorylating a protein. $^{32}$P-ATP is subsequently incorporated into the protein. Analysis of the phosphorylated protein may be performed by autoradiography. Other methods for measuring phosphorylation may involve isolating the phosphorylated protein by immunoprecipitation, followed by measurement of reactivity of the phosphorylated protein with a labeled phospho-threonine specific antibody. Antibodies specific for certain phosphorylated threonine residues may also be used directly on live cells with phosphorylated proteins on the cell surface or on whole cell lysates or a mixture of proteins after the lysates or the mixture of proteins are separated by electrophoresis and transferred to a membrane (e.g., PVDF or nitrocellulose in Western blots). Moreover, mass spectrometric techniques such as collision-induced dissociation (CID) and electron transfer dissociation (ETD) may also provide comprehensive parallel analysis of peptide sequences and phosphorylation.

Enzyme-linked immunosorbent assays (ELISAs) may also be used to measure phosphorylation. ELISA may be more quantitative than Western blotting. The format for this microplate-based assay typically utilizes a capture antibody specific for the desired protein, independent of the phosphorylation state in order to first capture the protein on the microplate. A detection antibody specific for the phosphorylation site to be analyzed is then added. These assays are typically designed using colorimetric or fluorometric detection. The intensity of the resulting signal is directly proportional to the concentration of phosphorylated protein present in the original sample. The results from ELISA are easily quantifiable by utilizing a calibrated standard. Further, high specificity is possible due to the use of two antibodies specific for the target protein employed together in the sandwich format. The higher sensitivity often accomplished using ELISAs may allow for smaller sample volumes and the detection of low abundance proteins. Finally, the microplate-based format also allows for much higher throughput than traditional Western blotting.

EXAMPLES

Example 1—Generating Trimeric Protein Complex p27-Cdk4-CycD Using an Engineered p27

Human Cdk4 variant (SEQ ID NO: 48), CycD1 variant (SEQ ID NO: 56), and engineered p27 (SEQ ID NO: 6 for amino acids 25-98 of p27 with Y74E) were co-expressed in Sf9 cells (Expression Systems, Davis, CA). Cells were simultaneously infected with three baculovirus vectors configured to express the Cdk4 variant, the CycD1 variant, and the engineered p27. Each baculovirus vector was generated using the pFastbac system, which utilizes the polyhedrin promoter. The Cdk4 variant and the engineered p27 were expressed as a GST fusion protein and the CycD1 variant was co-expressed untagged. Lysates were first purified by GS4B affinity chromatography (GE Healthcare). The protein complex was then eluted from the resin and subject to SOURCE 15Q anion exchange chromatography (GE Healthcare). The elution fraction from the anion exchange chromatography was then subjected to TEV protease cleavage overnight in 25 mM Tris, 200 mM NaCl, 1 mM DTT, and 0.5 mM EDTA (pH 8.0) at 4° C. The purified p27-Cdk4-CycD1 trimeric protein complex was then passed over GS4B affinity resin again to remove free GST. The p27-Cdk4-CycD1 trimeric protein complex was then concentrated, and stored in a buffer containing 20 mM Tris, 200 mM NaCl, 1 mM DTT, and 20% glycerol (pH 8.0).

Example 2—Generating Trimeric Protein Complex p27-Cdk4-CycD Using a Wild-Type p27

A dimer of Cdk4-CycD1 was first purified following the same protocol of expression and purification as described above, except the baculovirus vector configured to express p27 was left out of the initial infection. Engineered p27 (SEQ ID NO: 6 for amino acids 25-98 of p27 with Y74E) was expressed in *E. coli* as a fusion protein from a PGEX vector backbone containing T7 promoter. GST-p27 KID fusion was purified as described above.

In order to generate phosphorylated p27 KID, human Brk kinase was expressed in Sf9 cells as a GST fusion protein using the same pFastbac system (polyhedrin promoter). GST-Brk kinase fusion was purified as described above, except the GST fusion tag was not cut. About 100 mg p27 KID was treated with 10% GST-Brk kinase fusion (m/m) in a buffer containing 50 mM Tris, 150 mM NaCl, 1 mM DTT, 10 mM MgCl$_2$ and 1 mM ATP (pH 8.0) and incubated at 4° C. for 24 hours. The phosphorylated p27 was purified by passing through GS4B affinity resin to remove GST-Brk kinase and eluted from a Superdex 75 column (GE Healthcare) in a buffer containing 25 mM Tris, 100 mM NaCl, and 1 mM DTT, (pH 8.0). To form and reconstitute the Cdk4-CycD1-phosp27 trimeric protein complex, three-fold molar excess of phosp27 was mixed with the purified Cdk4-CycD1 dimeric complex. After incubation for 30 minutes on ice, the trimeric protein complex was purified from a Superdex 75 column (GE Healthcare) in a buffer containing 25 mM Tris, 100 mM NaCl, and 1 mM DTT, (pH 8.0).

Example 3—Kinase Assays

The phosphorylation activity of Cdk4 in various complexes was tested using different substrates. The protein complexes tested were:
(i) Cdk4-CycD1 dimeric complex (SEQ ID NO: 37 for wild-type Cdk4 and SEQ ID NO: 56 for CycD1 variant),
(ii) Cdk4-CycD1 dimeric complex (SEQ ID NO: 39 for Cdk4 variant having T172E substitution and SEQ ID NO: 56 for CycD1 variant),
(iii) wild-type p27-Cdk4-CycD1 trimeric complex with unphosphorylated p27 (SEQ ID NO: 1 for wild-type p27, SEQ ID NO: 37 for wild-type Cdk4 and SEQ ID NO: 56 for CycD1 variant),
(iv) wild-type p27-Cdk4-CycD1 trimeric complex with unphosphorylated p27 (SEQ ID NO: 1 for wild-type p27, SEQ ID NO: 39 for Cdk4 variant having T172E substitution and SEQ ID NO: 56 for CycD1 variant),
(v) wild-type p27-Cdk4-CycD1 trimeric complex with phosphorylated p27 (SEQ ID NO: 1 for wild-type p27, SEQ ID NO: 37 for wild-type Cdk4 and SEQ ID NO: 56 for CycD1 variant),
(vi) wild-type p27-Cdk4-CycD1 trimeric complex with phosphorylated p27 (SEQ ID NO: 1 for wild-type p27, SEQ ID NO: 37 for Cdk4 variant having T172E substitution and SEQ ID NO: 56 for CycD1 variant),
(vii) engineered p27-Cdk4-CycD1 trimeric complex (SEQ ID NO: 34 or 35 for full-length p27 with Y74E, Y88E, and Y89E, or for amino acids 25-106 of p27 with Y74E, Y88E, and Y89E, respectively, SEQ ID NO: 37 for wild-type Cdk4 and SEQ ID NO: 56 for CycD1 variant), and
(viii) engineered p27-Cdk4-CycD1 trimeric complex (SEQ ID NO: 34 or 35 for full-length p27 with Y74E, Y88E, and Y89E, or for amino acids 25-106 of p27 with Y74E, Y88E, and Y89E, respectively, SEQ ID NO: 37 for Cdk4 variant having T172E substitution and SEQ ID NO: 56 for CycD1 variant).

The substrates used in the kinase assays were the C-terminal domain of the retinoblastoma protein (Rb (771-928); SEQ ID NO: 62), the transactivation domain of FoxM1 (FoxM1 (526-748); SEQ ID NO: 64), and full-length histone H1 (SEQ ID NO: 65).

To observe kinase activity of the Cdk4 or variant thereof in the protein complexes described above, 0.5 µM protein complex was mixed with 20 µM substrate in a buffer containing 25 mM Tris, 200 mM NaCl, 10 mM MgCl$_2$, 1 mM DTT, 250 µM ATP, and 100 µCi of $^{32}$P-γ-ATP (pH 7.0). The substrate was diluted into the reaction buffer at the appropriate concentration, and the reaction was initiated through addition of the complex. The reaction was quenched after 30 minutes through addition of SDS-PAGE loading buffer.

Figure 1B:
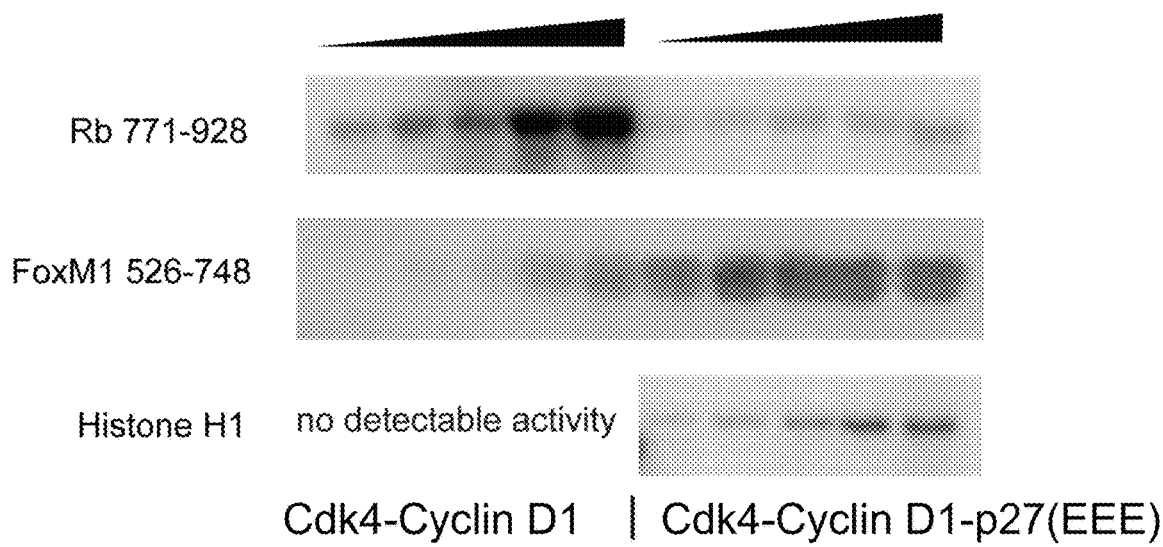
FIG. 1B shows steady-state kinetic assays measuring initial rate of phosphorylation as a function of ATP concentration for the indicated protein complex and substrate.

It was found that 1) Cdk4-CycD dimeric complex had high phosphorylation activity specifically for Rb; 2) the wild-type p27-Cdk4-CycD1 trimeric complex with unphosphorylated p27 (e.g., complexes (iii) and (iv) described above) was inhibited; and 3) the wild-type p27-Cdk4-CycD1 trimeric complex with phosphorylated p27 (e.g., complexes (v) and (vi) described above) and the engineered p27-Cdk4-CycD1 trimeric complex (e.g., complexes (vii) and (viii) described above) had phosphorylation activity toward all substrates. Through additional steady state kinetic analysis (FIGS. 1B and 1C), it was found that the engineered p27-Cdk4-CycD1 trimeric complex (e.g., complexes (vii) and (viii) described above) had a reduced KM for ATP. It was also found in a kinase assay that the wild-type p27-Cdk4-CycD1 trimeric complex with phosphorylated p27 and the engineered p27 with Y74E, Y88E, and Y89E-Cdk4-CycD1 trimeric complex were resistant to palbociclib inhibition (FIG. 1D). Compared to the data in FIG. 1D, which used recombinantly expressed proteins in a cell-free system, FIG. 1E shows that endogenous p27-Cdk4-CycD1 trimeric complex immunoprecipitated from cells was also not sensitive to palbociclib inhibition. Indicated cell lysates were immunoprecipitated with control or anti-p27 antibody, and the activity of the immunoprecipitate was used to phosphorylate Rb771-928 with $^{32}$P-ATP in the absence or presence of palbociclib. Reactions with the indicated recombinant dimer (K4D1/−) or trimer (K4D1/phosp27) enzymes are shown for comparison in the first four lanes of each SDS-PAGE gel in FIG. 1E. MCF7 and MDA-MB-231 cells are Rb-positive and palbociclib-sensitive breast cancer cells that differ in estrogen receptor status. T98G cells are glioma cells that are relatively less sensitive to palbociclib.

REFERENCES

1. Dick F A, Rubin S M. Molecular mechanisms underlying RB protein function. *Nat Rev Mol Cell Biol.* 2013; 14(5): 297-306. PubMed PMID: 23594950; PubMed Central PMCID: PMCPMC4754300.
2. Dyson N J. RB1: a prototype tumor suppressor and an enigma. *Genes Dev.* 2016; 30(13):1492-502. PubMed PMID: 27401552; PubMed Central PMCID: PMCPMC4949322.
3. Finn R S, Martin M, Rugo H S, Jones S, Im S A, Gelmon K, Harbeck N, Lipatov O N, Walshe J M, Moulder S, Gauthier E, Lu D R, Randolph S, Dieras V, Slamon D J. Palbociclib and Letrozole in Advanced Breast Cancer. *N Engl J Med.* 2016; 375(20):1925-36. PubMed PMID: 27959613.
4. Sherr C J. A New Cell-Cycle Target in Cancer—Inhibiting Cyclin D-Dependent Kinases 4 and 6. *N Engl J Med.* 2016; 375(20):1920-3. PubMed PMID: 27959598.
5. Sherr C J, Beach D, Shapiro G I. Targeting CDK4 and CDK6: From Discovery to Therapy. *Cancer Discov.* 2016; 6(4):353-67. PubMed PMID: 26658964; PubMed Central PMCID: PMCPMC4821753.
6. Dickler M N, Tolaney S M, Rugo H S, Cortes J, Dieras V, Patt D, Wildiers H, Hudis C A, O'Shaughnessy J, Zamora E, Yardley D A, Frenzel M, Koustenis A, Baselga J. MONARCH 1, A Phase II Study of Abemaciclib, a CDK4 and CDK6 Inhibitor, as a Single Agent, in Patients with Refractory H R(+)/HER2(−) Metastatic Breast Cancer. *Clin Cancer Res.* 2017; 23(17):5218-24. PubMed PMID: 28533223; PubMed Central PMCID: PMCPMC5581697.
7. He S, Roberts P J, Sorrentino J A, Bisi J E, Storrie-White H, Tiessen R G, Makhuli K M, Wargin W A, Tadema H, van Hoogdalem E J, Strum J C, Malik R, Sharpless N E. Transient CDK4/6 inhibition protects hematopoietic stem cells from chemotherapy-induced exhaustion. *Sci Transl Med.* 2017; 9(387). PubMed PMID: 28446688.
8. Xu H, Yu S, Liu Q, Yuan X, Mani S, Pestell R G, Wu K. Recent advances of highly selective CDK4/6 inhibitors in breast cancer. *J Hematol Oncol.* 2017; 10(1):97. PubMed PMID: 28438180; PubMed Central PMCID: PMCPMC5404666.
9. Bagui T K, Jackson R J, Agrawal D, Pledger W J. Analysis of cyclin D3-cdk4 complexes in fibroblasts expressing and lacking p27(kip1) and p21(cip1). *Mol Cell Biol.* 2000; 20(23):8748-57. PubMed PMID: 11073976; PubMed Central PMCID: PMCPMC86501.
10. Kato A, Takahashi H, Takahashi Y, Matsushime H. Inactivation of the cyclin D-dependent kinase in the rat fibroblast cell line, 3Y1, induced by contact inhibition. *J Biol Chem.* 1997; 272(12):8065-70. PubMed PMID: 9065480.
11. Kato J Y, Matsuoka M, Polyak K, Massague J, Sherr C J. Cyclic AMP-induced G1 phase arrest mediated by an inhibitor (p27Kip1) of cyclin-dependent kinase 4 activation. *Cell.* 1994; 79(3):487-96. PubMed PMID: 7954814.
12. Ladha M H, Lee K Y, Upton T M, Reed M F, Ewen M E. Regulation of exit from quiescence by p27 and cyclin D1-CDK4. *Mol Cell Biol.* 1998; 18(11):6605-15. PubMed PMID: 9774675; PubMed Central PMCID: PMCPMC109245.
13. Toyoshima H, Hunter T. p27, a novel inhibitor of G1 cyclin-Cdk protein kinase activity, is related to p21. *Cell.* 1994; 78(1):67-74. PubMed PMID: 8033213.
14. Bagui T K, Mohapatra S, Haura E, Pledger W J. P27Kip1 and p21Cip1 are not required for the formation of active D cyclin-cdk4 complexes. *Mol Cell Biol.* 2003; 23(20): 7285-90. PubMed PMID: 14517297; PubMed Central PMCID: PMCPMC230308.
15. Cheng M, Olivier P, Diehl J A, Fero M, Roussel M F, Roberts J M, Sherr C J. The p21(Cip1) and p27(Kip1) CDK 'inhibitors' are essential activators of cyclin D-dependent kinases in murine fibroblasts. *EMBO J.* 1999; 18(6):1571-83. PubMed PMID: 10075928; PubMed Central PMCID: PMCPMC1171245.
16. LaBaer J, Garrett M D, Stevenson L F, Slingerland J M, Sandhu C, Chou H S, Fattaey A, Harlow E. New functional activities for the p21 family of CDK inhibitors. *Genes Dev.* 1997; 11(7):847-62. PubMed PMID: 9106657.
17. Parry D, Mahony D, Wills K, Lees E. Cyclin D-CDK subunit arrangement is dependent on the availability of competing INK4 and p21 class inhibitors. *Mol Cell Biol.* 1999; 19(3):1775-83. PubMed PMID: 10022865; PubMed Central PMCID: PMCPMC83971.
18. Soos T J, Kiyokawa H, Yan J S, Rubin M S, Giordano A, DeBlasio A, Bottega S, Wong B, Mendelsohn J, Koff A. Formation of p27-CDK complexes during the human mitotic cell cycle. *Cell Growth Differ.* 1996; 7(2):135-46. PubMed PMID: 8822197.
19. Grimmler M, Wang Y, Mund T, Cilensek Z, Keidel E M, Waddell M B, Jakel H, Kullmann M, Kriwacki R W, Hengst L. Cdk-inhibitory activity and stability of p27Kip1 are directly regulated by oncogenic tyrosine kinases. *Cell.* 2007; 128(2):269-80. PubMed PMID: 17254966.
20. James M K, Ray A, Leznova D, Blain S W. Differential modification of p27Kip1 controls its cyclin D-cdk4 inhibitory activity. *Mol Cell Biol.* 2008; 28(1):498-510. PubMed PMID: 17908796; PubMed Central PMCID: PMCPMC2223302.
21. Patel P, Asbach B, Shteyn E, Gomez C, Coltoff A, Bhuyan S, Tyner A L, Wagner R, Blain S W. Brk/Protein tyrosine kinase 6 phosphorylates p27KIP1, regulating the activity of cyclin D-cyclin-dependent kinase 4. *Mol Cell Biol.* 2015; 35(9):1506-22. PubMed PMID: 25733683; PubMed Central PMCID: PMCPMC4387217.

SEQUENCE LISTING

```
Sequence total quantity: 73
SEQ ID NO: 1                moltype = AA  length = 198
FEATURE                     Location/Qualifiers
REGION                      1..198
                            note = Description of Unknown: p27 sequence
source                      1..198
                            mol_type = protein
                            organism = unidentified
SEQUENCE: 1
MSNVRVSNGS PSLERMDARQ AEHPKPSACR NLFGPVDHEE LTRDLEKHCR DMEEASQRKW   60
NFDFQNHKPL EGKYEWQEVE KGSLPEFYYR PPRPPKGACK VPAQESQDVS GSRPAAPLIG  120
APANSEDTHL VDPKTDPSDS QTGLAEQCAG IRKRPATDDS STQNKRANRT EENVSDGSPN  180
AGSVEQTPKK PGLRRRQT                                                198

SEQ ID NO: 2                moltype = AA  length = 82
FEATURE                     Location/Qualifiers
REGION                      1..82
                            note = Description of Unknown: p27 sequence
source                      1..82
                            mol_type = protein
                            organism = unidentified
SEQUENCE: 2
KPSACRNLFG PVDHEELTRD LEKHCRDMEE ASQRKWNFDF QNHKPLEGKY EWQEVEKGSL   60
PEFYYRPPRP PKGACKVPAQ ES                                            82

SEQ ID NO: 3                moltype = AA  length = 74
FEATURE                     Location/Qualifiers
REGION                      1..74
                            note = Description of Unknown: p27 sequence
source                      1..74
                            mol_type = protein
                            organism = unidentified
SEQUENCE: 3
KPSACRNLFG PVDHEELTRD LEKHCRDMEE ASQRKWNFDF QNHKPLEGKY EWQEVEKGSL   60
PEFYYRPPRP PKGA                                                     74

SEQ ID NO: 4                moltype = AA  length = 198
FEATURE                     Location/Qualifiers
REGION                      1..198
                            note = Description of Artificial Sequence: Synthetic
                             polypeptide
source                      1..198
                            mol_type = protein
                            organism = synthetic construct
SEQUENCE: 4
MSNVRVSNGS PSLERMDARQ AEHPKPSACR NLFGPVDHEE LTRDLEKHCR DMEEASQRKW   60
NFDFQNHKPL EGKEWQEVE KGSLPEFYYR PPRPPKGACK VPAQESQDVS GSRPAAPLIG   120
APANSEDTHL VDPKTDPSDS QTGLAEQCAG IRKRPATDDS STQNKRANRT EENVSDGSPN  180
AGSVEQTPKK PGLRRRQT                                                198

SEQ ID NO: 5                moltype = AA  length = 82
FEATURE                     Location/Qualifiers
REGION                      1..82
                            note = Description of Artificial Sequence: Synthetic
                             polypeptide
source                      1..82
                            mol_type = protein
                            organism = synthetic construct
SEQUENCE: 5
KPSACRNLFG PVDHEELTRD LEKHCRDMEE ASQRKWNFDF QNHKPLEGKE EWQEVEKGSL   60
PEFYYRPPRP PKGACKVPAQ ES                                            82

SEQ ID NO: 6                moltype = AA  length = 74
FEATURE                     Location/Qualifiers
REGION                      1..74
                            note = Description of Artificial Sequence: Synthetic
                             polypeptide
source                      1..74
                            mol_type = protein
                            organism = synthetic construct
SEQUENCE: 6
KPSACRNLFG PVDHEELTRD LEKHCRDMEE ASQRKWNFDF QNHKPLEGKE EWQEVEKGSL   60
PEFYYRPPRP PKGA                                                     74

SEQ ID NO: 7                moltype = AA  length = 198
FEATURE                     Location/Qualifiers
REGION                      1..198
                            note = Description of Artificial Sequence: Synthetic
```

```
                              polypeptide
source                        1..198
                              mol_type = protein
                              organism = synthetic construct
SEQUENCE: 7
MSNVRVSNGS PSLERMDARQ AEHPKPSACR NLFGPVDHEE LTRDLEKHCR DMEEASQRKW    60
NFDFQNHKPL EGKDEWQEVE KGSLPEFYYR PPRPPKGACK VPAQESQDVS GSRPAAPLIG   120
APANSEDTHL VDPKTDPSDS QTGLAEQCAG IRKRPATDDS STQNKRANRT EENVSDGSPN   180
AGSVEQTPKK PGLRRRQT                                                 198

SEQ ID NO: 8                  moltype = AA  length = 82
FEATURE                       Location/Qualifiers
REGION                        1..82
                              note = Description of Artificial Sequence: Synthetic
                               polypeptide
source                        1..82
                              mol_type = protein
                              organism = synthetic construct
SEQUENCE: 8
KPSACRNLFG PVDHEELTRD LEKHCRDMEE ASQRKWNFDF QNHKPLEGKD EWQEVEKGSL    60
PEFYYRPPRP PKGACKVPAQ ES                                            82

SEQ ID NO: 9                  moltype = AA  length = 74
FEATURE                       Location/Qualifiers
REGION                        1..74
                              note = Description of Artificial Sequence: Synthetic
                               polypeptide
source                        1..74
                              mol_type = protein
                              organism = synthetic construct
SEQUENCE: 9
KPSACRNLFG PVDHEELTRD LEKHCRDMEE ASQRKWNFDF QNHKPLEGKD EWQEVEKGSL    60
PEFYYRPPRP PKGA                                                     74

SEQ ID NO: 10                 moltype = AA  length = 198
FEATURE                       Location/Qualifiers
REGION                        1..198
                              note = Description of Artificial Sequence: Synthetic
                               polypeptide
source                        1..198
                              mol_type = protein
                              organism = synthetic construct
SEQUENCE: 10
MSNVRVSNGS PSLERMDARQ AEHPKPSACR NLFGPVDHEE LTRDLEKHCR DMEEASQRKW    60
NFDFQNHKPL EGKREWQEVE KGSLPEFYYR PPRPPKGACK VPAQESQDVS GSRPAAPLIG   120
APANSEDTHL VDPKTDPSDS QTGLAEQCAG IRKRPATDDS STQNKRANRT EENVSDGSPN   180
AGSVEQTPKK PGLRRRQT                                                 198

SEQ ID NO: 11                 moltype = AA  length = 82
FEATURE                       Location/Qualifiers
REGION                        1..82
                              note = Description of Artificial Sequence: Synthetic
                               polypeptide
source                        1..82
                              mol_type = protein
                              organism = synthetic construct
SEQUENCE: 11
KPSACRNLFG PVDHEELTRD LEKHCRDMEE ASQRKWNFDF QNHKPLEGKR EWQEVEKGSL    60
PEFYYRPPRP PKGACKVPAQ ES                                            82

SEQ ID NO: 12                 moltype = AA  length = 74
FEATURE                       Location/Qualifiers
REGION                        1..74
                              note = Description of Artificial Sequence: Synthetic
                               polypeptide
source                        1..74
                              mol_type = protein
                              organism = synthetic construct
SEQUENCE: 12
KPSACRNLFG PVDHEELTRD LEKHCRDMEE ASQRKWNFDF QNHKPLEGKR EWQEVEKGSL    60
PEFYYRPPRP PKGA                                                     74

SEQ ID NO: 13                 moltype = AA  length = 198
FEATURE                       Location/Qualifiers
REGION                        1..198
                              note = Description of Artificial Sequence: Synthetic
                               polypeptide
source                        1..198
                              mol_type = protein
```

```
                              organism = synthetic construct
SEQUENCE: 13
MSNVRVSNGS PSLERMDARQ AEHPKPSACR NLFGPVDHEE LTRDLEKHCR DMEEASQRKW    60
NFDFQNHKPL EGKYEWQEVE KGSLPEFEYR PPRPPKGACK VPAQESQDVS GSRPAAPLIG   120
APANSEDTHL VDPKTDPSDS QTGLAEQCAG IRKRPATDDS STQNKRANRT EENVSDGSPN   180
AGSVEQTPKK PGLRRRQT                                                198

SEQ ID NO: 14             moltype = AA  length = 82
FEATURE                   Location/Qualifiers
REGION                    1..82
                          note = Description of Artificial Sequence: Synthetic
                            polypeptide
source                    1..82
                          mol_type = protein
                          organism = synthetic construct
SEQUENCE: 14
KPSACRNLFG PVDHEELTRD LEKHCRDMEE ASQRKWNFDF QNHKPLEGKY EWQEVEKGSL    60
PEFEYRPPRP PKGACKVPAQ ES                                            82

SEQ ID NO: 15             moltype = AA  length = 74
FEATURE                   Location/Qualifiers
REGION                    1..74
                          note = Description of Artificial Sequence: Synthetic
                            polypeptide
source                    1..74
                          mol_type = protein
                          organism = synthetic construct
SEQUENCE: 15
KPSACRNLFG PVDHEELTRD LEKHCRDMEE ASQRKWNFDF QNHKPLEGKY EWQEVEKGSL    60
PEFEYRPPRP PKGA                                                     74

SEQ ID NO: 16             moltype = AA  length = 198
FEATURE                   Location/Qualifiers
REGION                    1..198
                          note = Description of Artificial Sequence: Synthetic
                            polypeptide
source                    1..198
                          mol_type = protein
                          organism = synthetic construct
SEQUENCE: 16
MSNVRVSNGS PSLERMDARQ AEHPKPSACR NLFGPVDHEE LTRDLEKHCR DMEEASQRKW    60
NFDFQNHKPL EGKYEWQEVE KGSLPEFDYR PPRPPKGACK VPAQESQDVS GSRPAAPLIG   120
APANSEDTHL VDPKTDPSDS QTGLAEQCAG IRKRPATDDS STQNKRANRT EENVSDGSPN   180
AGSVEQTPKK PGLRRRQT                                                198

SEQ ID NO: 17             moltype = AA  length = 82
FEATURE                   Location/Qualifiers
REGION                    1..82
                          note = Description of Artificial Sequence: Synthetic
                            polypeptide
source                    1..82
                          mol_type = protein
                          organism = synthetic construct
SEQUENCE: 17
KPSACRNLFG PVDHEELTRD LEKHCRDMEE ASQRKWNFDF QNHKPLEGKY EWQEVEKGSL    60
PEFDYRPPRP PKGACKVPAQ ES                                            82

SEQ ID NO: 18             moltype = AA  length = 74
FEATURE                   Location/Qualifiers
REGION                    1..74
                          note = Description of Artificial Sequence: Synthetic
                            polypeptide
source                    1..74
                          mol_type = protein
                          organism = synthetic construct
SEQUENCE: 18
KPSACRNLFG PVDHEELTRD LEKHCRDMEE ASQRKWNFDF QNHKPLEGKY EWQEVEKGSL    60
PEFDYRPPRP PKGA                                                     74

SEQ ID NO: 19             moltype = AA  length = 198
FEATURE                   Location/Qualifiers
REGION                    1..198
                          note = Description of Artificial Sequence: Synthetic
                            polypeptide
source                    1..198
                          mol_type = protein
                          organism = synthetic construct
SEQUENCE: 19
MSNVRVSNGS PSLERMDARQ AEHPKPSACR NLFGPVDHEE LTRDLEKHCR DMEEASQRKW    60
```

```
NFDFQNHKPL EGKYEWQEVE KGSLPEFYER PPRPPKGACK VPAQESQDVS GSRPAAPLIG    120
APANSEDTHL VDPKTDPSDS QTGLAEQCAG IRKRPATDDS STQNKRANRT EENVSDGSPN    180
AGSVEQTPKK PGLRRRQT                                                  198

SEQ ID NO: 20            moltype = AA   length = 82
FEATURE                  Location/Qualifiers
REGION                   1..82
                         note = Description of Artificial Sequence: Synthetic
                          polypeptide
source                   1..82
                         mol_type = protein
                         organism = synthetic construct
SEQUENCE: 20
KPSACRNLFG PVDHEELTRD LEKHCRDMEE ASQRKWNFDF QNHKPLEGKY EWQEVEKGSL    60
PEFYERPPRP PKGACKVPAQ ES                                             82

SEQ ID NO: 21            moltype = AA   length = 74
FEATURE                  Location/Qualifiers
REGION                   1..74
                         note = Description of Artificial Sequence: Synthetic
                          polypeptide
source                   1..74
                         mol_type = protein
                         organism = synthetic construct
SEQUENCE: 21
KPSACRNLFG PVDHEELTRD LEKHCRDMEE ASQRKWNFDF QNHKPLEGKY EWQEVEKGSL    60
PEFYERPPRP PKGA                                                      74

SEQ ID NO: 22            moltype = AA   length = 198
FEATURE                  Location/Qualifiers
REGION                   1..198
                         note = Description of Artificial Sequence: Synthetic
                          polypeptide
source                   1..198
                         mol_type = protein
                         organism = synthetic construct
SEQUENCE: 22
MSNVRVSNGS PSLERMDARQ AEHPKPSACR NLFGPVDHEE LTRDLEKHCR DMEEASQRKW    60
NFDFQNHKPL EGKYEWQEVE KGSLPEFYDR PPRPPKGACK VPAQESQDVS GSRPAAPLIG    120
APANSEDTHL VDPKTDPSDS QTGLAEQCAG IRKRPATDDS STQNKRANRT EENVSDGSPN    180
AGSVEQTPKK PGLRRRQT                                                  198

SEQ ID NO: 23            moltype = AA   length = 82
FEATURE                  Location/Qualifiers
REGION                   1..82
                         note = Description of Artificial Sequence: Synthetic
                          polypeptide
source                   1..82
                         mol_type = protein
                         organism = synthetic construct
SEQUENCE: 23
KPSACRNLFG PVDHEELTRD LEKHCRDMEE ASQRKWNFDF QNHKPLEGKY EWQEVEKGSL    60
PEFYDRPPRP PKGACKVPAQ ES                                             82

SEQ ID NO: 24            moltype = AA   length = 74
FEATURE                  Location/Qualifiers
REGION                   1..74
                         note = Description of Artificial Sequence: Synthetic
                          polypeptide
source                   1..74
                         mol_type = protein
                         organism = synthetic construct
SEQUENCE: 24
KPSACRNLFG PVDHEELTRD LEKHCRDMEE ASQRKWNFDF QNHKPLEGKY EWQEVEKGSL    60
PEFYDRPPRP PKGA                                                      74

SEQ ID NO: 25            moltype = AA   length = 198
FEATURE                  Location/Qualifiers
REGION                   1..198
                         note = Description of Artificial Sequence: Synthetic
                          polypeptide
source                   1..198
                         mol_type = protein
                         organism = synthetic construct
SEQUENCE: 25
MSNVRVSNGS PSLERMDARQ AEHPKPSACR NLFGPVDHEE LTRDLEKHCR DMEEASQRKW    60
NFDFQNHKPL EGKEEWQEVE KGSLPEFYER PPRPPKGACK VPAQESQDVS GSRPAAPLIG    120
APANSEDTHL VDPKTDPSDS QTGLAEQCAG IRKRPATDDS STQNKRANRT EENVSDGSPN    180
AGSVEQTPKK PGLRRRQT                                                  198
```

```
SEQ ID NO: 26           moltype = AA  length = 82
FEATURE                 Location/Qualifiers
REGION                  1..82
                        note = Description of Artificial Sequence: Synthetic
                         polypeptide
source                  1..82
                        mol_type = protein
                        organism = synthetic construct
SEQUENCE: 26
KPSACRNLFG PVDHEELTRD LEKHCRDMEE ASQRKWNFDF QNHKPLEGKE EWQEVEKGSL    60
PEFEYRPPRP PKGACKVPAQ ES                                            82

SEQ ID NO: 27           moltype = AA  length = 74
FEATURE                 Location/Qualifiers
REGION                  1..74
                        note = Description of Artificial Sequence: Synthetic
                         polypeptide
source                  1..74
                        mol_type = protein
                        organism = synthetic construct
SEQUENCE: 27
KPSACRNLFG PVDHEELTRD LEKHCRDMEE ASQRKWNFDF QNHKPLEGKE EWQEVEKGSL    60
PEFEYRPPRP PKGA                                                     74

SEQ ID NO: 28           moltype = AA  length = 198
FEATURE                 Location/Qualifiers
REGION                  1..198
                        note = Description of Artificial Sequence: Synthetic
                         polypeptide
source                  1..198
                        mol_type = protein
                        organism = synthetic construct
SEQUENCE: 28
MSNVRVSNGS PSLERMDARQ AEHPKPSACR NLFGPVDHEE LTRDLEKHCR DMEEASQRKW    60
NFDFQNHKPL EGKEEWQEVE KGSLPEFEYR PPRPPKGACK VPAQESQDVS GSRPAAPLIG   120
APANSEDTHL VDPKTDPSDS QTGLAEQCAG IRKRPATDDS STQNKRANRT EENVSDGSPN   180
AGSVEQTPKK PGLRRRQT                                                198

SEQ ID NO: 29           moltype = AA  length = 82
FEATURE                 Location/Qualifiers
REGION                  1..82
                        note = Description of Artificial Sequence: Synthetic
                         polypeptide
source                  1..82
                        mol_type = protein
                        organism = synthetic construct
SEQUENCE: 29
KPSACRNLFG PVDHEELTRD LEKHCRDMEE ASQRKWNFDF QNHKPLEGKE EWQEVEKGSL    60
PEFYERPPRP PKGACKVPAQ ES                                            82

SEQ ID NO: 30           moltype = AA  length = 74
FEATURE                 Location/Qualifiers
REGION                  1..74
                        note = Description of Artificial Sequence: Synthetic
                         polypeptide
source                  1..74
                        mol_type = protein
                        organism = synthetic construct
SEQUENCE: 30
KPSACRNLFG PVDHEELTRD LEKHCRDMEE ASQRKWNFDF QNHKPLEGKE EWQEVEKGSL    60
PEFYERPPRP PKGA                                                     74

SEQ ID NO: 31           moltype = AA  length = 198
FEATURE                 Location/Qualifiers
REGION                  1..198
                        note = Description of Artificial Sequence: Synthetic
                         polypeptide
source                  1..198
                        mol_type = protein
                        organism = synthetic construct
SEQUENCE: 31
MSNVRVSNGS PSLERMDARQ AEHPKPSACR NLFGPVDHEE LTRDLEKHCR DMEEASQRKW    60
NFDFQNHKPL EGKYEWQEVE KGSLPEFEER PPRPPKGACK VPAQESQDVS GSRPAAPLIG   120
APANSEDTHL VDPKTDPSDS QTGLAEQCAG IRKRPATDDS STQNKRANRT EENVSDGSPN   180
AGSVEQTPKK PGLRRRQT                                                198

SEQ ID NO: 32           moltype = AA  length = 82
FEATURE                 Location/Qualifiers
```

```
REGION                        1..82
                              note = Description of Artificial Sequence: Synthetic
                               polypeptide
source                        1..82
                              mol_type = protein
                              organism = synthetic construct
SEQUENCE: 32
KPSACRNLFG PVDHEELTRD LEKHCRDMEE ASQRKWNFDF QNHKPLEGKY EWQEVEKGSL      60
PEFEERPPRP PKGACKVPAQ ES                                              82

SEQ ID NO: 33                 moltype = AA   length = 74
FEATURE                       Location/Qualifiers
REGION                        1..74
                              note = Description of Artificial Sequence: Synthetic
                               polypeptide
source                        1..74
                              mol_type = protein
                              organism = synthetic construct
SEQUENCE: 33
KPSACRNLFG PVDHEELTRD LEKHCRDMEE ASQRKWNFDF QNHKPLEGKY EWQEVEKGSL      60
PEFEERPPRP PKGA                                                       74

SEQ ID NO: 34                 moltype = AA   length = 198
FEATURE                       Location/Qualifiers
REGION                        1..198
                              note = Description of Artificial Sequence: Synthetic
                               polypeptide
source                        1..198
                              mol_type = protein
                              organism = synthetic construct
SEQUENCE: 34
MSNVRVSNGS PSLERMDARQ AEHPKPSACR NLFGPVDHEE LTRDLEKHCR DMEEASQRKW      60
NFDFQNHKPL EGKEEWQEVE KGSLPEFEER PPRPPKGACK VPAQESQDVS GSRPAAPLIG     120
APANSEDTHL VDPKTDPSDS QTGLAEQCAG IRKRPATDDS STQNKRANRT EENVSDGSPN     180
AGSVEQTPKK PGLRRRQT                                                  198

SEQ ID NO: 35                 moltype = AA   length = 82
FEATURE                       Location/Qualifiers
REGION                        1..82
                              note = Description of Artificial Sequence: Synthetic
                               polypeptide
source                        1..82
                              mol_type = protein
                              organism = synthetic construct
SEQUENCE: 35
KPSACRNLFG PVDHEELTRD LEKHCRDMEE ASQRKWNFDF QNHKPLEGKE EWQEVEKGSL      60
PEFEERPPRP PKGACKVPAQ ES                                              82

SEQ ID NO: 36                 moltype = AA   length = 74
FEATURE                       Location/Qualifiers
REGION                        1..74
                              note = Description of Artificial Sequence: Synthetic
                               polypeptide
source                        1..74
                              mol_type = protein
                              organism = synthetic construct
SEQUENCE: 36
KPSACRNLFG PVDHEELTRD LEKHCRDMEE ASQRKWNFDF QNHKPLEGKE EWQEVEKGSL      60
PEFEERPPRP PKGA                                                       74

SEQ ID NO: 37                 moltype = AA   length = 303
FEATURE                       Location/Qualifiers
REGION                        1..303
                              note = Description of Unknown: Cdk4 sequence
source                        1..303
                              mol_type = protein
                              organism = unidentified
SEQUENCE: 37
MATSRYEPVA EIGVGAYGTV YKARDPHSGH FVALKSVRVP NGGGGGGGLP ISTVREVALL      60
RRLEAFEHPN VVRLMDVCAT SRTDREIKVT LVFEHVDQDL RTYLDKAPPP GLPAETIKDL     120
MRQFLRGLDF LHANCIVHRD LKPENILVTS GGTVKLADFG LARIYSYQMA LTPVVVTLWY     180
RAPEVLLQST YATPVDMWSV GCIFAEMFRR KPLFCGNSEA DQLGKIFDLI GLPPEDDWPR     240
DVSLPRGAFP PRGPRPVQSV VPEMEESGAQ LLLEMLTFNP HKRISAFRAL QHSYLHKDEG     300
NPE                                                                  303

SEQ ID NO: 38                 moltype = AA   length = 303
FEATURE                       Location/Qualifiers
REGION                        1..303
                              note = Description of Artificial Sequence: Synthetic
```

```
                        polypeptide
source                  1..303
                        mol_type = protein
                        organism = synthetic construct
SEQUENCE: 38
MATSRYEPVA EIGVGAYGTV YKARDPHSGH FVALKSVRVP NGGGGGGGLP ISTVREVALL    60
RRLEAFEHPN VVRLMDVCAT SRTDREIKVT LVFEHVDQDL RTYLDKAPPP GLPAETIKDL   120
MRQFLRGLDF LHANCIVHRD LKPENILVTS GGTVKLADFG LARIYSYQMA LDPVVVTLWY   180
RAPEVLLQST YATPVDMWSV GCIFAEMFRR KPLFCGNSEA DQLGKIFDLI GLPPEDDWPR   240
DVSLPRGAFP PRGPRPVQSV VPEMEESGAQ LLLEMLTFNP HKRISAFRAL QHSYLHKDEG   300
NPE                                                                 303

SEQ ID NO: 39           moltype = AA   length = 303
FEATURE                 Location/Qualifiers
REGION                  1..303
                        note = Description of Artificial Sequence: Synthetic
                        polypeptide
source                  1..303
                        mol_type = protein
                        organism = synthetic construct
SEQUENCE: 39
MATSRYEPVA EIGVGAYGTV YKARDPHSGH FVALKSVRVP NGGGGGGGLP ISTVREVALL    60
RRLEAFEHPN VVRLMDVCAT SRTDREIKVT LVFEHVDQDL RTYLDKAPPP GLPAETIKDL   120
MRQFLRGLDF LHANCIVHRD LKPENILVTS GGTVKLADFG LARIYSYQMA LEPVVVTLWY   180
RAPEVLLQST YATPVDMWSV GCIFAEMFRR KPLFCGNSEA DQLGKIFDLI GLPPEDDWPR   240
DVSLPRGAFP PRGPRPVQSV VPEMEESGAQ LLLEMLTFNP HKRISAFRAL QHSYLHKDEG   300
NPE                                                                 303

SEQ ID NO: 40           moltype = AA   length = 300
FEATURE                 Location/Qualifiers
REGION                  1..300
                        note = Description of Artificial Sequence: Synthetic
                        polypeptide
source                  1..300
                        mol_type = protein
                        organism = synthetic construct
SEQUENCE: 40
MATSRYEPVA EIGVGAYGTV YKARDPHSGH FVALKSVRVP NGEEGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALTP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 41           moltype = AA   length = 300
FEATURE                 Location/Qualifiers
REGION                  1..300
                        note = Description of Artificial Sequence: Synthetic
                        polypeptide
source                  1..300
                        mol_type = protein
                        organism = synthetic construct
SEQUENCE: 41
MATSRYEPVA EIGVGAYGTV YKARDPHSGH FVALKSVRVP NGDEGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALTP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 42           moltype = AA   length = 300
FEATURE                 Location/Qualifiers
REGION                  1..300
                        note = Description of Artificial Sequence: Synthetic
                        polypeptide
source                  1..300
                        mol_type = protein
                        organism = synthetic construct
SEQUENCE: 42
MATSRYEPVA EIGVGAYGTV YKARDPHSGH FVALKSVRVP NGEDGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALTP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 43           moltype = AA   length = 300
FEATURE                 Location/Qualifiers
REGION                  1..300
                        note = Description of Artificial Sequence: Synthetic
                        polypeptide
source                  1..300
```

```
                        mol_type = protein
                        organism = synthetic construct
SEQUENCE: 43
MATSRYEPVA EIGVGAYGTV YKARDPHSGH FVALKSVRVP NGDDGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALTP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 44           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 44
MATSRYEPVA EIGVGAYGTV YKARDPHSGH FVALKSVRVP NGEEGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALDP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 45           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 45
MATSRYEPVA EIGVGAYGTV YKARDPHSGH FVALKSVRVP NGDEGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALDP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 46           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 46
MATSRYEPVA EIGVGAYGTV YKARDPHSGH FVALKSVRVP NGEDGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALDP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 47           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 47
MATSRYEPVA EIGVGAYGTV YKARDPHSGH FVALKSVRVP NGDDGLPIST VREVALLRRL    60
EAFEHPNVVR LMDVCATSRT DREIKVTLVF EHVDQDLRTY LDKAPPPGLP AETIKDLMRQ   120
FLRGLDFLHA NCIVHRDLKP ENILVTSGGT VKLADFGLAR IYSYQMALDP VVVTLWYRAP   180
EVLLQSTYAT PVDMWSVGCI FAEMFRRKPL FCGNSEADQL GKIFDLIGLP PEDDWPRDVS   240
LPRGAFPPRG PRPVQSVVPE MEESGAQLLL EMLTFNPHKR ISAFRALQHS YLHKDEGNPE   300

SEQ ID NO: 48           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 48
MATSRYEPVA EIGVGAYGTV YKARDPHSGH FVALKSVRVP NGEEGLPIST VREVALLRRL    60
```

```
EAFEHPNVVR LMDVCATSRT DREIKVTLVF EHVDQDLRTY LDKAPPPGLP AETIKDLMRQ    120
FLRGLDFLHA NCIVHRDLKP ENILVTSGGT VKLADFGLAR IYSYQMALEP VVVTLWYRAP    180
EVLLQSTYAT PVDMWSVGCI FAEMFRRKPL FCGNSEADQL GKIFDLIGLP PEDDWPRDVS    240
LPRGAFPPRG PRPVQSVVPE MEESGAQLLL EMLTFNPHKR ISAFRALQHS YLHKDEGNPE    300

SEQ ID NO: 49           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 49
MATSRYEPVA EIGVGAYGTV YKARDPHSGH FVALKSVRVP NGDEGLPIST VREVALLRRL     60
EAFEHPNVVR LMDVCATSRT DREIKVTLVF EHVDQDLRTY LDKAPPPGLP AETIKDLMRQ    120
FLRGLDFLHA NCIVHRDLKP ENILVTSGGT VKLADFGLAR IYSYQMALEP VVVTLWYRAP    180
EVLLQSTYAT PVDMWSVGCI FAEMFRRKPL FCGNSEADQL GKIFDLIGLP PEDDWPRDVS    240
LPRGAFPPRG PRPVQSVVPE MEESGAQLLL EMLTFNPHKR ISAFRALQHS YLHKDEGNPE    300

SEQ ID NO: 50           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 50
MATSRYEPVA EIGVGAYGTV YKARDPHSGH FVALKSVRVP NGEDGLPIST VREVALLRRL     60
EAFEHPNVVR LMDVCATSRT DREIKVTLVF EHVDQDLRTY LDKAPPPGLP AETIKDLMRQ    120
FLRGLDFLHA NCIVHRDLKP ENILVTSGGT VKLADFGLAR IYSYQMALEP VVVTLWYRAP    180
EVLLQSTYAT PVDMWSVGCI FAEMFRRKPL FCGNSEADQL GKIFDLIGLP PEDDWPRDVS    240
LPRGAFPPRG PRPVQSVVPE MEESGAQLLL EMLTFNPHKR ISAFRALQHS YLHKDEGNPE    300

SEQ ID NO: 51           moltype = AA   length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 51
MATSRYEPVA EIGVGAYGTV YKARDPHSGH FVALKSVRVP NGDDGLPIST VREVALLRRL     60
EAFEHPNVVR LMDVCATSRT DREIKVTLVF EHVDQDLRTY LDKAPPPGLP AETIKDLMRQ    120
FLRGLDFLHA NCIVHRDLKP ENILVTSGGT VKLADFGLAR IYSYQMALEP VVVTLWYRAP    180
EVLLQSTYAT PVDMWSVGCI FAEMFRRKPL FCGNSEADQL GKIFDLIGLP PEDDWPRDVS    240
LPRGAFPPRG PRPVQSVVPE MEESGAQLLL EMLTFNPHKR ISAFRALQHS YLHKDEGNPE    300

SEQ ID NO: 52           moltype = AA   length = 326
FEATURE                 Location/Qualifiers
REGION                  1..326
                        note = Description of Unknown: Cdk6 sequence
source                  1..326
                        mol_type = protein
                        organism = unidentified
SEQUENCE: 52
MEKDGLCRAD QQYECVAEIG EGAYGKVFKA RDLKNGGRFV ALKRVRVQTG EEGMPLSTIR     60
EVAVLRHLET FEHPNVVRLF DVCTVSRTDR ETKLTLVFEH VDQDLTTYLD KVPEPGVPTE    120
TIKDMMFQLL RGLDFLHSHR VVHRDLKPQN ILVTSSGQIK LADFGLARIY SFQMALTSVV    180
VTLWYRAPEV LLQSSYATPV DLWSVGCIFA EMFRRKPLFR GSSDVDQLGK ILDVIGLPGE    240
EDWPRDVALP RQAFHSKSAQ PIEKFVTDID ELGKDLLLKC LTFNPAKRIS AYSALSHPYF    300
QDLERCKENL DSHLPPSQNT SELNTA                                         326

SEQ ID NO: 53           moltype = AA   length = 326
FEATURE                 Location/Qualifiers
REGION                  1..326
                        note = Description of Artificial Sequence: Synthetic
                         polypeptide
source                  1..326
                        mol_type = protein
                        organism = synthetic construct
SEQUENCE: 53
MEKDGLCRAD QQYECVAEIG EGAYGKVFKA RDLKNGGRFV ALKRVRVQTG EEGMPLSTIR     60
EVAVLRHLET FEHPNVVRLF DVCTVSRTDR ETKLTLVFEH VDQDLTTYLD KVPEPGVPTE    120
TIKDMMFQLL RGLDFLHSHR VVHRDLKPQN ILVTSSGQIK LADFGLARIY SFQMALDSVV    180
VTLWYRAPEV LLQSSYATPV DLWSVGCIFA EMFRRKPLFR GSSDVDQLGK ILDVIGLPGE    240
EDWPRDVALP RQAFHSKSAQ PIEKFVTDID ELGKDLLLKC LTFNPAKRIS AYSALSHPYF    300
```

```
QDLERCKENL DSHLPPSQNT SELNTA                                           326

SEQ ID NO: 54          moltype = AA  length = 326
FEATURE                Location/Qualifiers
REGION                 1..326
                       note = Description of Artificial Sequence: Synthetic
                       polypeptide
source                 1..326
                       mol_type = protein
                       organism = synthetic construct
SEQUENCE: 54
MEKDGLCRAD QQYECVAEIG EGAYGKVFKA RDLKNGGRFV ALKRVRVQTG EEGMPLSTIR       60
EVAVLRHLET FEHPNVVRLF DVCTVSRTDR ETKLTLVFEH VDQDLTTYLD KVPEPGVPTE      120
TIKDMMFQLL RGLDFLHSHR VVHRDLKPQN ILVTSSGQIK LADFGLARIY SFQMALESVV      180
VTLWYRAPEV LLQSSYATPV DLWSVGCIFA EMFRRKPLFR GSSDVDQLGK ILDVIGLPGE      240
EDWPRDVALP RQAFHSKSAQ PIEKFVTDID ELGKDLLLKC LTFNPAKRIS AYSALSHPYF      300
QDLERCKENL DSHLPPSQNT SELNTA                                           326

SEQ ID NO: 55          moltype = AA  length = 295
FEATURE                Location/Qualifiers
REGION                 1..295
                       note = Description of Unknown: CycD1 sequence
source                 1..295
                       mol_type = protein
                       organism = unidentified
SEQUENCE: 55
MEHQLLCCEV ETIRRAYPDA NLLNDRVLRA MLKAEETCAP SVSYFKCVQK EVLPSMRKIV       60
ATWMLEVCEE QKCEEEVFPL AMNYLDRFLS LEPVKKSRLQ LLGATCMFVA SKMKETIPLT      120
AEKLCIYTDN SIRPEELLQM ELLLVNKLKW NLAAMTPHDF IEHFLSKMPE AEEENKQIIRK     180
HAQTFVALCA TDVKFISNPP SMVAAGSVVA AVQGLNLRSP NNFLSYYRLT RPLSRVIKCD      240
PDCLRACQEQ IEALLESSLR QAQQNMDPKA AEEEEEEEEE VDLACTPTDV RDVDI           295

SEQ ID NO: 56          moltype = AA  length = 249
FEATURE                Location/Qualifiers
REGION                 1..249
                       note = Description of Unknown: CycD1 sequence
source                 1..249
                       mol_type = protein
                       organism = unidentified
SEQUENCE: 56
DANLLNDRVL RAMLKAEETC APSVSYFKCV QKEVLPSMRK IVATWMLEVC EEQKCEEEVF       60
PLAMNYLDRF LSLEPVKKSR LQLLGATCMF VASKMKETIP LTAEKLCIYT DNSIRPEELL      120
QMELLLVNKL KWNLAAMTPH DFIEHFLSKM PEAEENKQII RKHAQTFVAL CATDVKFISN      180
PPSMVAAGSV VAAVQGLNLR SPNNFLSYYR LTRFLSRVIK CDPDCLRACQ EQIEALLESS      240
LRQAQQNMD                                                              249

SEQ ID NO: 57          moltype = AA  length = 289
FEATURE                Location/Qualifiers
REGION                 1..289
                       note = Description of Unknown: CycD2 sequence
source                 1..289
                       mol_type = protein
                       organism = unidentified
SEQUENCE: 57
MELLCHEVDP VRRAVRDRNL LRDDRVLQNL LTIEERYLPQ CSYFKCVQKD IQPYMRRMVA       60
TWMLEVCEEQ KCEEEVFPLA MNYLDRFLAG VPTPKSHLQL LGAVCMFLAS KLKETSPLTA      120
EKLCIYTDNS IKPQELLEWE LVVLGKLKWN LAAVTPHDFI EHILRKLPQQ REKLSLIRKH      180
AQTFIALCAT DFKFAMYPPS MIATGSVGAA ICGLQQDEEV SSLTCDALTE LLAKITNTDV      240
DCLKACQEQI EAVLLNSLQQ YRQDQRDGSK SEDELDQAST PTDVRDIDL                  289

SEQ ID NO: 58          moltype = AA  length = 292
FEATURE                Location/Qualifiers
REGION                 1..292
                       note = Description of Unknown: CycD3 sequence
source                 1..292
                       mol_type = protein
                       organism = unidentified
SEQUENCE: 58
MELLCCEGTR HAPRAGPDPR LLGDQRVLQS LLRLEERYVP RASYFQCVQR EIKPHMRKML       60
AYWMLEVCEE QRCEEEVFPL AMNYLDRYLS CVPTRKAQLQ LLGAVCMLLA SKLRETTPLT      120
IEKLCIYTDH AVSPRQLRDW EVLVLGKLKW DLAAVIAHDF LAFILHRLSL PRDRQALVKK      180
HAQTFLALCA TDYTFAMYPP SMIATGSIGA AVQGLGACSM SGDELTELLA GITGTEVDCL      240
RACQEQIEAA LRESLREASQ TSSSPAPKAP RGSSSQGPSQ TSTPTDVTAI HL              292

SEQ ID NO: 59          moltype = AA  length = 74
FEATURE                Location/Qualifiers
REGION                 1..74
                       note = Description of Artificial Sequence: Synthetic
                       polypeptide
```

```
VARIANT             50
                    note = X can be Y, E, D or R
                    note = At least one of the X's present at location 50,64
                     and 65 in the given sequence is not Y
VARIANT             64
                    note = X can be Y, E or D
                    note = At least one of the X's present at location 50,64
                     and 65 in the given sequence is not Y
VARIANT             65
                    note = X can be Y, E or D
                    note = At least one of the X's present at location 50,64
                     and 65 in the given sequence is not Y
REGION              1..74
                    note = See specification as filed for detailed description
                     of substitutions and preferred embodiments
source              1..74
                    mol_type = protein
                    organism = synthetic construct
SEQUENCE: 59
KPSACRNLFG PVDHEELTRD LEKHCRDMEE ASQRKWNFDF QNHKPLEGKX EWQEVEKGSL    60
PEFXXRPPRP PKGA                                                    74

SEQ ID NO: 60       moltype =   length =
SEQUENCE: 60
000

SEQ ID NO: 61       moltype = AA   length = 928
FEATURE             Location/Qualifiers
REGION              1..928
                    note = Description of Unknown: Rb sequence
source              1..928
                    mol_type = protein
                    organism = unidentified
SEQUENCE: 61
MPPKTPRKTA ATAAAAAAEP PAPPPPPPPE EDPEQDSGPE DLPLVRLEFE ETEEPDFTAL    60
CQKLKIPDHV RERAWLTWEK VSSVDGVLGG YIQKKKELWG ICIFIAAVDL DEMSFTFTEL   120
QKNIEISVHK FFNLLKEIDT STKVDNAMSR LLKKYDVLFA LFSKLERTCE LIYLTQPSSS   180
ISTEINSALV LKVSWITFLL AKGEVLQMED DLVISFQLML CVLDYFIKLS PPMLLKEPYK   240
TAVIPINGSP RTPRRGQNRS ARIAKQLEND TRIIEVLCKE HECNIDEVKN VYFKNFIPFM   300
NSLGLVTSNG LPEVENLSKR YEEIYLKNKD LDARLFLDHD KTLQTDSIDS FETQRTPRKS   360
NLDEEVNVIP PHTPVRTVMN TIQQLMMILN SASDQPSENL ISYFNNCTVN PKESILKRVK   420
DIGYIFKEKF AKAVGQGCVE IGSQRYKLGV RLYYRVMESM LKSEEERLSI QNFSKLLNDN   480
IFHMSLLACA LEVVMATYSR STSQNLDSGT DLSFPWILNV LNLKAFDFYK VIESFIKAEG   540
NLTREMIKHL ERCEHRIMES LAWLSDSPLF DLIKQSKDRE GPTDHLESAC PLNLPLQNNH   600
TAADMYLSPV RSPKKKGSTT RVNSTANAET QATSAFQTQK PLKSTSLSLF YKKVYRLAYL   660
RLNTLCERLL SEHPELEHII WTLFQHTLQN EYELMRDRHL DQIMMCSMYG ICKVKNIDLK   720
FKIIVTAYKD LPHAVQETFK RVLIKEEEYD SIIVFYNSVF MQRLKTNILQ YASTRPPTLS   780
PIPHIPRSPY KFPSSPLRIP GGNIYISPLK SPYKISEGLP TPTKMTPRSR ILVSIGESFG   840
TSEKFQKINQ MVCNSDRVLK RSAEGSNPPK PLKKLRFDIE GSDEADGSKH LPGESKFQQK   900
LAEMTSTRTR MQKQKMNDSM DTSNKEEK                                    928

SEQ ID NO: 62       moltype = AA   length = 158
FEATURE             Location/Qualifiers
REGION              1..158
                    note = Description of Unknown: Rb sequence
source              1..158
                    mol_type = protein
                    organism = unidentified
SEQUENCE: 62
YASTRPPTLS PIPHIPRSPY KFPSSPLRIP GGNIYISPLK SPYKISEGLP TPTKMTPRSR    60
ILVSIGESFG TSEKFQKINQ MVCNSDRVLK RSAEGSNPPK PLKKLRFDIE GSDEADGSKH   120
LPGESKFQQK LAEMTSTRTR MQKQKMNDSM DTSNKEEK                          158

SEQ ID NO: 63       moltype = AA   length = 763
FEATURE             Location/Qualifiers
REGION              1..763
                    note = Description of Unknown: FoxM1 sequence
source              1..763
                    mol_type = protein
                    organism = unidentified
SEQUENCE: 63
MKTSPRRPLI LKRRRLPLPV QNAPSETSEE EPKRSPAQQE SNQAEASKEV AESNSCKFPA    60
GIKIINHPTM PNTQVVAIPN NANIHSIITA LTAKGKESGS SGPNKFILIS CGGAPTQPPG   120
LRPQTQTSYD AKRTEVTLET LGPKPAARDV NLPRPPGALC EQKRETCADG EAAGCTINNS   180
LSNIQWLRKM SSDGLGSRSI KQEMEEKENC HLEQRQVKVE EPSRPASWQ NSVSERPPYS   240
YMAMIQFAIN STERKRMTLK DIYTWIEDHF PYFKHIAKPG WKNSIRHNLS LHDMFVRETS   300
ANGKVSFWTI HPSANRYLTL DQVFKPLDPG SPQLPEHLES QQKRPNPELR RNMTIKTELP   360
LGARRKMKPL LPRVSSYLVP IQFPVNQSLV LQPSVKVPLP LAASLMSSEL ARHSKRVRIA   420
PKVLLAEEGI APLSSAGPGK EEKLLFGEGF SPLLPVQTIK EEEIQPGEEM PHLARPIKVE   480
```

```
SPPLEEWPSP APSFKEESSH SWEDSSQSPT PRPKKSYSGL RSPTRCVSEM LVIQHRERRE    540
RSRSRRKQHL LPPCVDEPEL LFSEGPSTSR WAAELPFPAD SSDPASQLSY SQEVGGPFKT    600
PIKETLPISS TPSKSVLPRT PESWRLTPPA KVGGLDFSPV QTSQGASDPL PDPLGLMDLS    660
TTPLQSAPPL ESPQRLLSSE PLDLISVPFG NSSPSDIDVP KPGSPEPQVS GLAANRSLTE    720
GLVLDTMNDS LSKILLDISF PGLDEDPLGP DNINWSQFIP ELQ                      763

SEQ ID NO: 64           moltype = AA   length = 223
FEATURE                 Location/Qualifiers
REGION                  1..223
                        note = Description of Unknown: FoxM1 sequence
source                  1..223
                        mol_type = protein
                        organism = unidentified
SEQUENCE: 64
CVSEMLVIQH RERRERSRSR RKQHLLPPCV DEPELLFSEG PSTSRWAAEL PFPADSSDPA     60
SQLSYSQEVG GPFKTPIKET LPISSTPSKS VLPRTPESWR LTPPAKVGGL DFSPVQTSQG    120
ASDPLPDPLG LMDLSTTPLQ SAPPLESPQR LLSSEPLDLI SVPFGNSSPS DIDVPKPGSP    180
EPQVSGLAAN RSLTEGLVLD TMNDSLSKIL LDISFPGLDE DPL                      223

SEQ ID NO: 65           moltype = AA   length = 215
FEATURE                 Location/Qualifiers
REGION                  1..215
                        note = Description of Unknown: Histone H1 sequence
source                  1..215
                        mol_type = protein
                        organism = unidentified
SEQUENCE: 65
MSETVPPAPA ASAAPEKPLA GKKAKKPAKA AAASKKKPAG PSVSELIVQA ASSSKERGGV     60
SLAALKKALA AAGYDVEKNN SRIKLGIKSL VSKGTLVQTK GTGASGSFKL NKKASSVETK    120
PGASKVATKT KATGASKKLK KATGASKKSV KTPKKAKKPA ATRKSSKNPK KPKTVKPKKV    180
AKSPAKAKAV KPKAAKARVT KPKTAKPKKA APKKK                               215

SEQ ID NO: 66           moltype = AA   length = 6
FEATURE                 Location/Qualifiers
REGION                  1..6
                        note = Description of Artificial Sequence: Synthetic 6xHis
                        tag
source                  1..6
                        mol_type = protein
                        organism = synthetic construct
SEQUENCE: 66
HHHHHH                                                                 6

SEQ ID NO: 67           moltype = AA   length = 7
FEATURE                 Location/Qualifiers
REGION                  1..7
                        note = Description of Unknown: TEV protease cleavage
                        sequence
source                  1..7
                        mol_type = protein
                        organism = unidentified
SEQUENCE: 67
ENLYFQG                                                                7

SEQ ID NO: 68           moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 68
DYKDDDDK                                                               8

SEQ ID NO: 69           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 69
EQKLISEEDL                                                            10

SEQ ID NO: 70           moltype = AA   length = 9
FEATURE                 Location/Qualifiers
REGION                  1..9
                        note = Description of Artificial Sequence: Synthetic peptide
source                  1..9
```

```
                         mol_type = protein
                         organism = synthetic construct
SEQUENCE: 70
YPYDVPDYA                                                              9

SEQ ID NO: 71            moltype = AA  length = 24
FEATURE                  Location/Qualifiers
REGION                   1..24
                         note = Description of Artificial Sequence: Synthetic peptide
source                   1..24
                         mol_type = protein
                         organism = synthetic construct
SEQUENCE: 71
DYKDDDDKDY KDDDDKDYKD DDDK                                            24

SEQ ID NO: 72            moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 72
EQKLISEEDL EQKLISEEDL EQKLISEEDL                                      30

SEQ ID NO: 73            moltype = AA  length = 27
FEATURE                  Location/Qualifiers
REGION                   1..27
                         note = Description of Artificial Sequence: Synthetic peptide
source                   1..27
                         mol_type = protein
                         organism = synthetic construct
SEQUENCE: 73
YPYDVPDYAY PYDVPDYAYP YDVPDYA                                         27
```

What is claimed:

1. A trimeric protein complex comprising:
   (i) a polypeptide comprising an engineered p27, wherein the engineered p27 comprises amino acid substitutions at positions Y74, Y88, and Y89, wherein the amino acid substitution at position Y74 is Y74E, Y74D, or Y74R, the amino acid substitution at Y88 is Y88E or Y88D, and the amino acid substitution at Y89 is Y89E or Y89D, wherein the amino acid positions are determined with reference to the sequence of SEQ ID NO: 1, and wherein the engineered p27 has at least 90% sequence identity to SEQ ID NO: 1;
   (ii) a Cdk4 or a variant thereof, or a Cdk6 or a variant thereof; and
   (iii) a CycD or a variant thereof,
      wherein the Cdk4 or the variant thereof or the Cdk6 or the variant thereof in the trimeric protein complex is an active kinase.

2. The trimeric protein complex of claim 1, wherein the Cdk4 or the variant thereof or the Cdk6 or the variant thereof is capable of phosphorylating a protein comprising a phosphorylation site having the sequence X1PX2X3, wherein X1 is S or T; X2 is any amino acid; and X3 is K or R.

3. The trimeric protein complex of claim 2, wherein the protein is retinoblastoma protein (Rb), FoxM1, or histone H1.

4. The trimeric protein complex of claim 1, wherein the CycD is CycD1, CycD2, CycD3, or a variant thereof.

5. The trimeric protein complex of claim 4, wherein the CycD1 or the variant thereof comprises a sequence having at least 90% sequence identity to the sequence of (SEQ ID NO: 55)
MEHQLLCCEVETIRRAYPDANLLNDRVLRAMLKAEETCAPSVSYFKCVQK
EVLPSMRKIVATWMLEVCEEQKCEEEVFPLAMNYLDRFLSLEPVKKSRLQ
LLGATCMFVASKMKETIPLTAEKLCIYTDNSIRPEELLQMELLLVNKLKW
NLAAMTPHDFIEHFLSKMPEAEENKQIIRKHAQTFVALCATDVKFISNPP
SMVAAGSVVAAVQGLNLRSPNNFLSYYRLTRFLSRVIKCDPDCLRACQEQ
IEALLESSLRQAQQNMDPKAAEEEEEEEEVDLACTPTDVRDVDI,
or (SEQ ID NO: 56)
DANLLNDRVLRAMLKAEETCAPSVSYFKCVQKEVLPSMRKIVATWMLEVC
EEQKCEEEVFPLAMNYLDRFLSLEPVKKSRLQLLGATCMFVASKMKETIP
LTAEKLCIYTDNSIRPEELLQMELLLVNKLKWNLAAMTPHDFIEHFLSKM
PEAEENKQIIRKHAQTFVALCATDVKFISNPPSMVAAGSVVAAVQGLNLR
SPNNFLSYYRLTRFLSRVIKCDPDCLRACQEQIEALLESSLRQAQQNMD.

6. The trimeric protein complex of claim 4, wherein the CycD2 comprises a sequence having at least 90% sequence identity to the sequence of (SEQ ID NO: 57)
MELLCHEVDPVRRAVRDRNLLRDDRVLQNLLTIEERYLPQCSYEKCVQKDI
QPYMRRMVATWMLEVCEEQKCEEEVFPLAMNYLDRFLAGVPTPKSHLQLLG -continued

AVCMFLASKLKETSPLTAEKLCIYTDNSIKPQELLEWELVVLGKLKWNLAA

VTPHDFIEHILRKLPQQREKLSLIRKHAQTFIALCATDFKFAMYPPSMIAT

GSVGAAICGLQQDEEVSSLTCDALTELLAKITNTDVDCLKACQEQIEAVLL

NSLQQYRQDQRDGSKSEDELDQASTPTDVRDIDL.

7. The trimeric protein complex of claim 4, wherein the CycD3 comprises a sequence having at least 90% sequence identity to the sequence of (SEQ ID NO: 58)
MELLCCEGTRHAPRAGPDPRLLGDQRVLQSLLRLEERYVPRASYFQCVQRE

IKPHMRKMLAYWMLEVCEEQRCEEEVFPLAMNYLDRYLSCVPTRKAQLQLL

GAVCMLLASKLRETTPLTIEKLCIYTDHAVSPRQLRDWEVLVLGKLKWDLA

AVIAHDFLAFILHRLSLPRDRQALVKKHAQTFLALCATDYTFAMYPPSMIA

TGSIGAAVQGLGACSMSGDELTELLAGITGTEVDCLRACQEQIEAALRESL

REASQTSSSPAPKAPRGSSSQGPSQTSTPTDVTAIHL.

8. The trimeric protein complex of claim 1, wherein the Cdk4 comprises a sequence having at least 90% sequence identity to the sequence of (SEQ ID NO: 37)
MATSRYEPVAEIGVGAYGTVYKARDPHSGHFVALKSVRVPNGGGGGGLPI

STVREVALLRRLEAFEHPNVVRLMDVCATSRTDREIKVTLVFEHVDQDLRT

YLDKAPPPGLPAETIKDLMRQFLRGLDFLHANCIVHRDLKPENILVTSGGT

VKLADFGLARIYSYQMALTPVVVTLWYRAPEVLLQSTYATPVDMWSVGCIF

AEMFRRKPLFCGNSEADQLGKIFDLIGLPPEDDWPRDVSLPRGAFPPRGPR

PVQSVVPEMEESGAQLLLEMLTFNPHKRISAFRALQHSYLHKDEGNPE.

9. The trimeric protein complex of claim 1, wherein the variant of Cdk4 comprises T172E or T172D, and wherein the amino acid positions are determined with reference to the sequence of SEQ ID NO: 37.

10. The trimeric protein complex of claim 9, wherein the variant of Cdk4 comprises a sequence having at least 90% sequence identity to the sequence of (SEQ ID NO: 39)
MATSRYEPVAEIGVGAYGTVYKARDPHSGHFVALKSVRVPNGGGGGGLP

ISTVREVALLRRLEAFEHPNVVRLMDVCATSRTDREIKVTLVFEHVDQDL

RTYLDKAPPPGLPAETIKDLMRQFLRGLDFLHANCIVHRDLKPENILVTS

GGTVKLADFGLARIYSYQMALEPVVVTLWYRAPEVLLQSTYATPVDMWSV

GCIFAEMFRRKPLFCGNSEADQLGKIFDLIGLPPEDDWPRDVSLPRGAFP

PRGPRPVQSVVPEMEESGAQLLLEMLTFNPHKRISAFRALQHSYLHKDEG

NPE,
or (SEQ ID NO: 38)
MATSRYEPVAEIGVGAYGTVYKARDPHSGHFVALKSVRVPNGGGGGGLP

ISTVREVALLRRLEAFEHPNVVRLMDVCATSRTDREIKVTLVFEHVDQDL

RTYLDKAPPPGLPAETIKDLMRQFLRGLDFLHANCIVHRDLKPENILVTS

GGTVKLADFGLARIYSYQMALDPVVVTLWYRAPEVLLQSTYATPVDMWSV

-continued

GCIFAEMFRRKPLFCGNSEADQLGKIFDLIGLPPEDDWPRDVSLPRGAFP

PRGPRPVQSVVPEMEESGAQLLLEMLTFNPHKRISAFRALQHSYLHKDEG

NPE.

11. The trimeric protein complex of claim 1, wherein the variant of Cdk4 has amino acid residues 44 to 46 deleted, G43E or G43D, and G47E or G47D, and wherein the amino acid positions are determined with reference to the sequence of SEQ ID NO: 37.

12. The trimeric protein complex of claim 11, wherein the variant of Cdk4 comprises a sequence having at least 90% sequence identity to the sequence of (SEQ ID NO: 42)
MATSRYEPVAEIGVGAYGTVYKARDPHSGHFVALKSVRVPNGEDGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALTPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E, (SEQ ID NO: 41)
MATSRYEPVAEIGVGAYGTVYKARDPHSGHFVALKSVRVPNGDEGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALTPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E, (SEQ ID NO: 40)
MATSRYEPVAEIGVGAYGTVYKARDPHSGHFVALKSVRVPNGEEGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALTPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E,
or (SEQ ID NO: 43)
MATSRYEPVAEIGVGAYGTVYKARDPHSGHFVALKSVRVPNGDDGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALTPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E.

13. The trimeric protein complex of claim 1, wherein the variant of Cdk4 has amino acid residues 44 to 46 deleted, G43E or G43D, G47E or G47D, and T172E or T172D, wherein the amino acid positions are determined with reference to the sequence of SEQ ID NO: 37.

14. The trimeric protein complex of claim 1, wherein the variant of Cdk4 comprises a sequence having at least 90% sequence identity to the sequence of

```
                                    (SEQ ID NO: 48)
MATSRYEPVAEIGVGAYGTVYKARDPHSGHFVALKSVRVPNGEEGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALEPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E,
or
                                    (SEQ ID NO: 44)
MATSRYEPVAEIGVGAYGTVYKARDPHSGHFVALKSVRVPNGEEGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALDPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E.
```

15. The trimeric protein complex of claim 1, wherein the Cdk6 comprises a sequence having at least 90% sequence identity to the sequence of

```
                                    (SEQ ID NO: 52)
MEKDGLCRADQQYECVAEIGEGAYGKVFKARDLKNGGRFVALKRVRVQTG

EEGMPLSTIREVAVLRHLETFEHPNVVRLFDVCTVSRTDRETKLTLVFEH

VDQDLTTYLDKVPEPGVPTETIKDMMFQLLRGLDFLHSHRVVHRDLKPQN

ILVTSSGQIKLADFGLARIYSFQMALTSVVVTLWYRAPEVLLQSSYATPV

DLWSVGCIFAEMFRRKPLFRGSSDVDQLGKILDVIGLPGEEDWPRDVALP

RQAFHSKSAQPIEKFVTDIDELGKDLLLKCLTFNPAKRISAYSALSHPYF

QDLERCKENLDSHLPPSQNTSELNTA.
```

16. The trimeric protein complex of claim 1, wherein the variant of Cdk6 comprises T177E or T177D, and wherein the amino acid positions are determined with reference to the sequence of SEQ ID NO: 52.

17. The trimeric protein complex of claim 16, the variant of Cdk6 comprises a sequence having at least 90% sequence identity to the sequence of

```
                                    (SEQ ID NO: 54)
MEKDGLCRADQQYECVAEIGEGAYGKVFKARDLKNGGRFVALKRVRVQTG

EEGMPLSTIREVAVLRHLETFEHPNVVRLFDVCTVSRTDRETKLTLVFEH

VDQDLTTYLDKVPEPGVPTETIKDMMFQLLRGLDFLHSHRVVHRDLKPQN

ILVTSSGQIKLADFGLARIYSFQMALESVVVTLWYRAPEVLLQSSYATPV

DLWSVGCIFAEMFRRKPLFRGSSDVDQLGKILDVIGLPGEEDWPRDVALP

RQAFHSKSAQPIEKFVTDIDELGKDLLLKCLTFNPAKRISAYSALSHPYF

QDLERCKENLDSHLPPSQNTSELNTA,
or
                                    (SEQ ID NO: 53)
MEKDGLCRADQQYECVAEIGEGAYGKVFKARDLKNGGRFVALKRVRVQTG

EEGMPLSTIREVAVLRHLETFEHPNVVRLFDVCTVSRTDRETKLTLVFEH

VDQDLTTYLDKVPEPGVPTETIKDMMFQLLRGLDFLHSHRVVHRDLKPQN

ILVTSSGQIKLADFGLARIYSFQMALDSVVVTLWYRAPEVLLQSSYATPV

DLWSVGCIFAEMFRRKPLFRGSSDVDQLGKILDVIGLPGEEDWPRDVALP

RQAFHSKSAQPIEKFVTDIDELGKDLLLKCLTFNPAKRISAYSALSHPYF

QDLERCKENLDSHLPPSQNTSELNTA.
```

18. The trimeric protein complex of claim 1, wherein the engineered p27 comprises a sequence of

```
                                    (SEQ ID NO: 59)
KPSACRNLFGPVDHEELTRDLEKHCRDMEEASQRKWNFDFQNHKPLEGK

X1EWQEVEKGSLPEFX2X3RPPRPPKGA,
``` wherein X1 is E, D, or R; X2 is E, orD; and X3 is E, or D.

19. The trimeric protein complex of claim 1, wherein the engineered p27 comprises a sequence having at least 90% sequence identity to a sequence comprising SEQ ID NO: 36 or 34.

* * * * *